United States Patent [19]

Wilson et al.

[11] Patent Number: 4,764,367
[45] Date of Patent: Aug. 16, 1988

[54] USE OF $C_8$-T-ALKANOLS AND $C_5$-$C_{11}$-OMEGA-ALKEN-1-OLS IN ATTRACTING INSECTS

[75] Inventors: Richard A. Wilson, Westfield; Braja D. Mookherjee, Holmdel, both of N.J.; Jerry F. Butler, Gainesville, Fla.; Donald A. Withycombe, deceased, late of Lincroft, N.J., by Janet L. Withycombe, executrix; Ira Katz, West Long Branch, N.J.; Kenneth R. Schrankel, Tinton Falls, N.J.

[73] Assignees: International Flavors & Fragrances Inc., New York, N.Y.; The University of Florida, Gainesville, Fla.

[21] Appl. No.: 86,907

[22] Filed: Aug. 19, 1987

Related U.S. Application Data

[63] Continuation-in-part of Ser. No. 2,023, Jan. 9, 1987, which is a continuation-in-part of Ser. No. 879,426, Jun. 27, 1986, Pat. No. 4,693,890.

[51] Int. Cl.⁴ ...................... A01N 25/00; A01N 25/10
[52] U.S. Cl. ........................................ 424/84; 424/77; 424/78
[58] Field of Search .................... 424/84, 78, 77

[56] References Cited

U.S. PATENT DOCUMENTS

| | | | |
|---|---|---|---|
| 1,572,568 | 2/1926 | Smith et al. | 424/84 |
| 3,852,419 | 12/1974 | Roelofs et al. | 424/84 |
| 4,042,681 | 8/1977 | Underhill et al. | 424/84 |
| 4,152,422 | 5/1979 | Ohinata et al. | 424/84 |
| 4,447,659 | 5/1984 | Blewett | 568/913 |

OTHER PUBLICATIONS

Beroza and Green, "Materials Tested as Insect Attractants", Agriculture Handbook, No. 239, Ag. Res. Service, USDA, Washington, D.C., Jun. 1963, pp. 70-73.
"Chemosystematics and Evolution of Beetle Chemical Defenses", Annual Rev. of Entomology, vol. 32, 1987, Mittler et al, pp. 17-48.

Primary Examiner—William R. Dixon, Jr.
Assistant Examiner—David M. Brunsman
Attorney, Agent, or Firm—Arthur L. Liberman

[57] ABSTRACT

Described are the uses of $C_8$-t-alkanols and $C_5$-$C_{11}$-omega-alken-1-ols taken alone or taken in combination as attractants house flies (*Musca domestica L.* (Diptera:-Muscidae)). The $C_8$-t-alkanols and $C_5$-$C_{11}$-omega-alken-1-ols taken alone or in combination find utility primarily as bait enhancers for acute toxins and/or trapping devices.

13 Claims, 36 Drawing Sheets

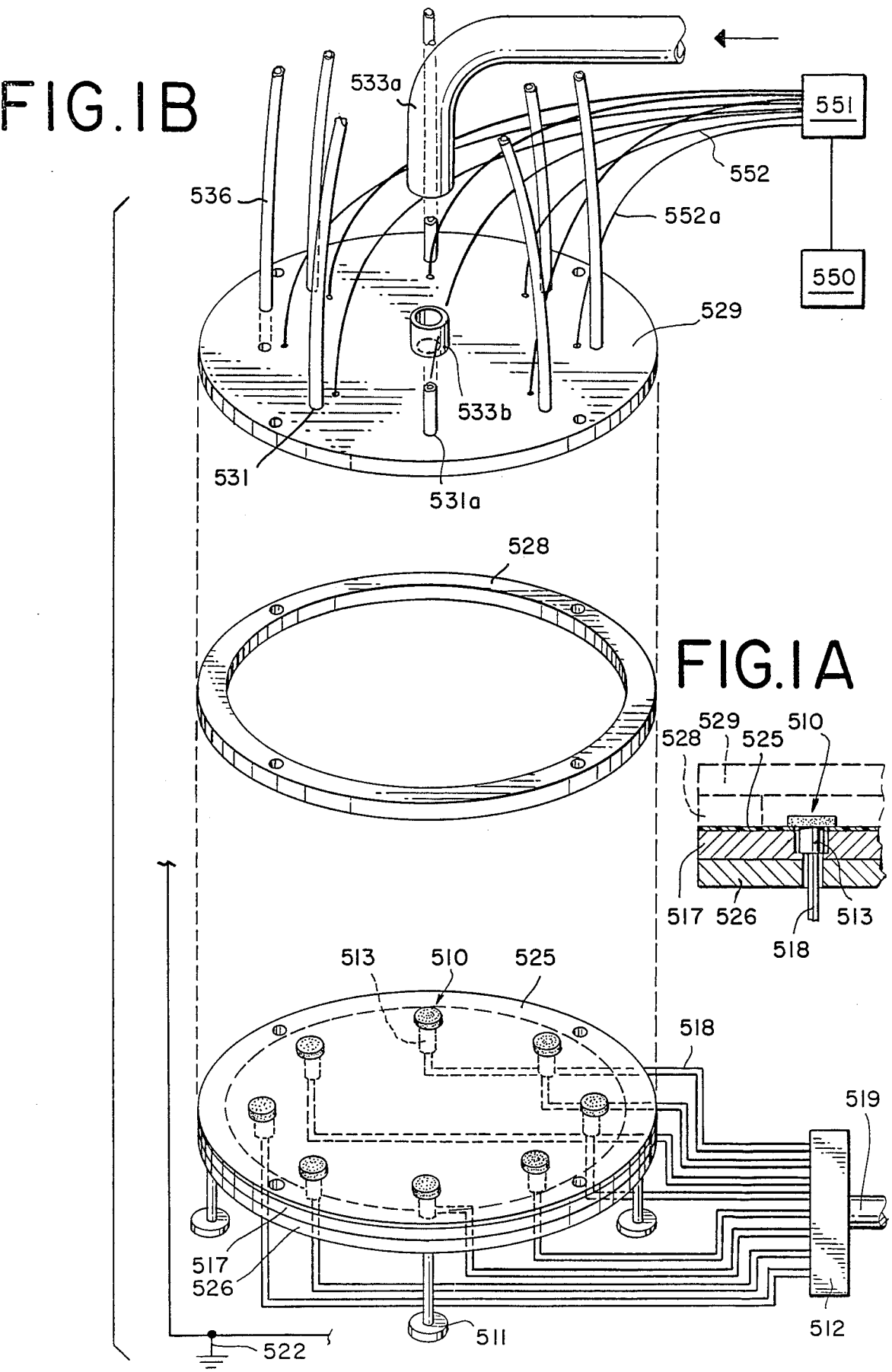

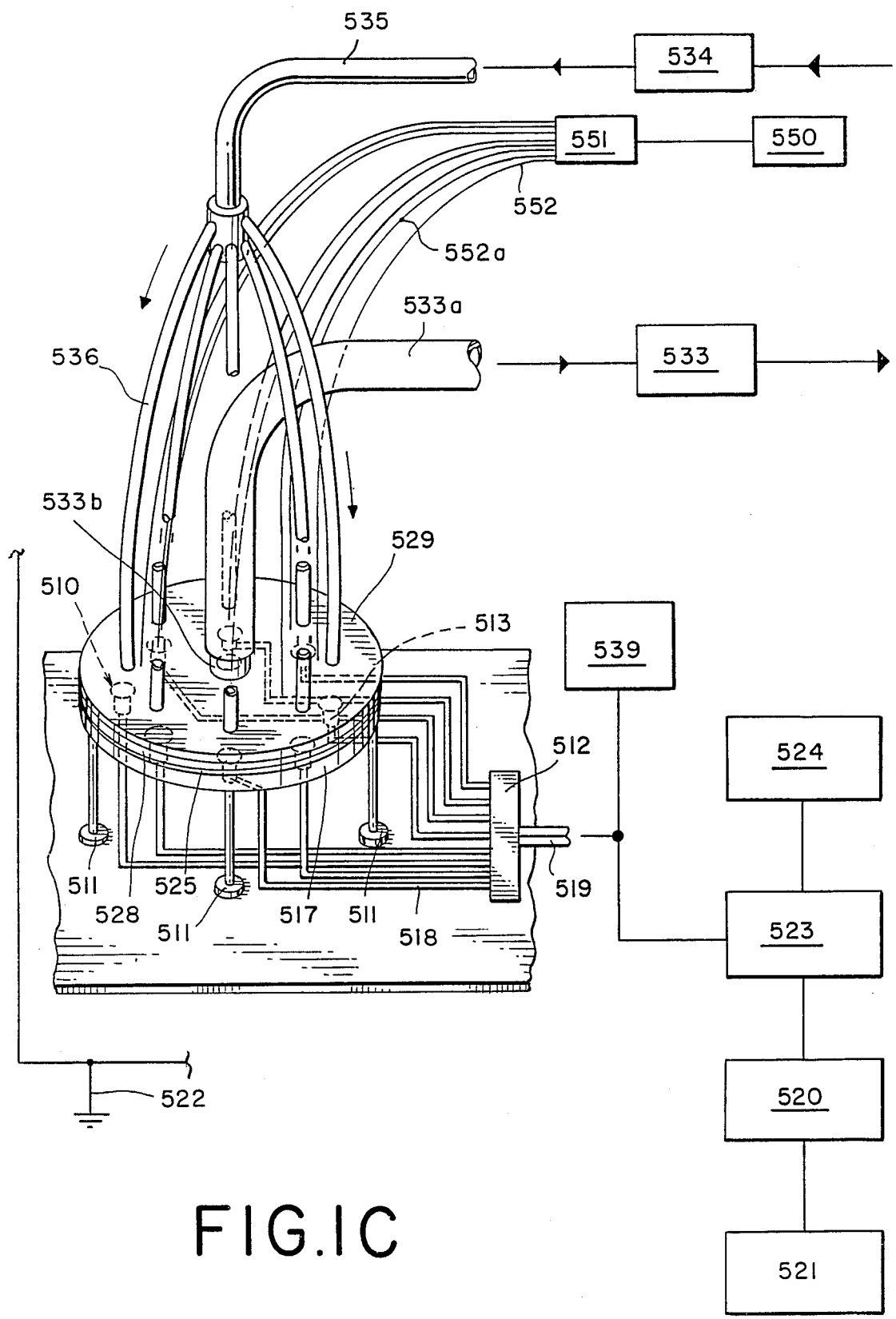
FIG.IC

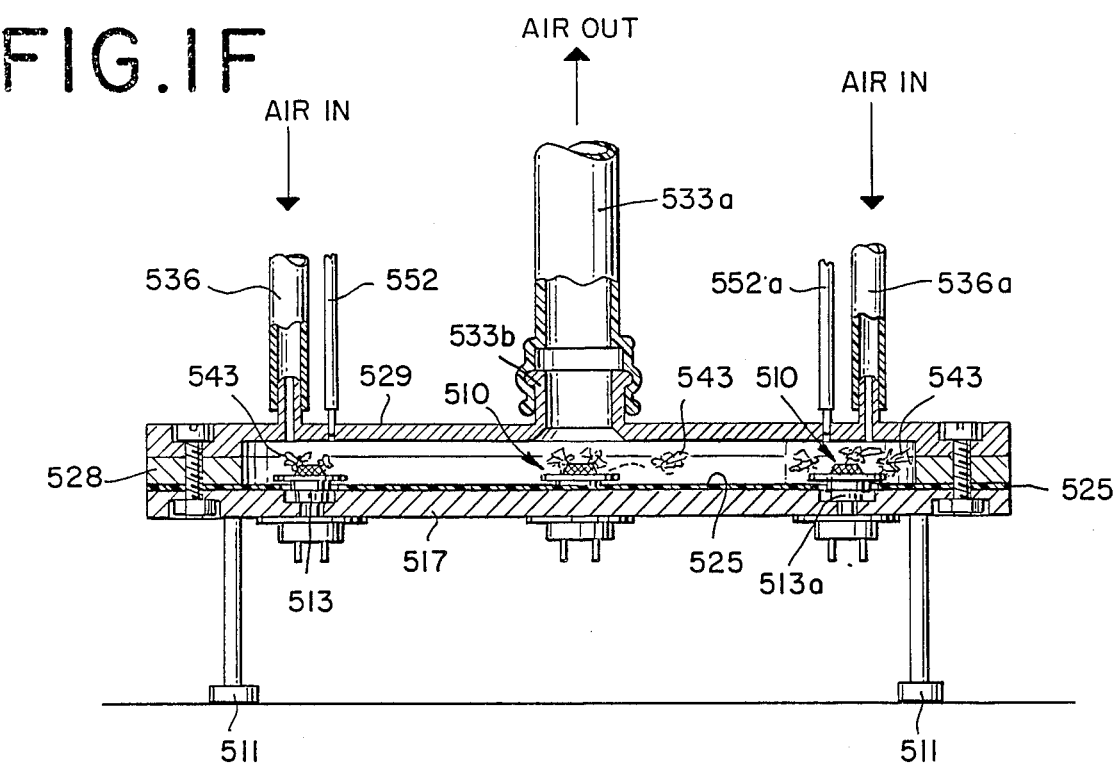
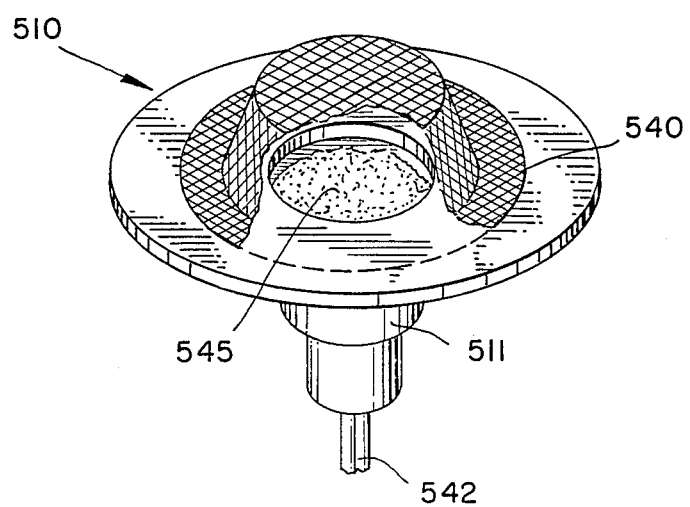

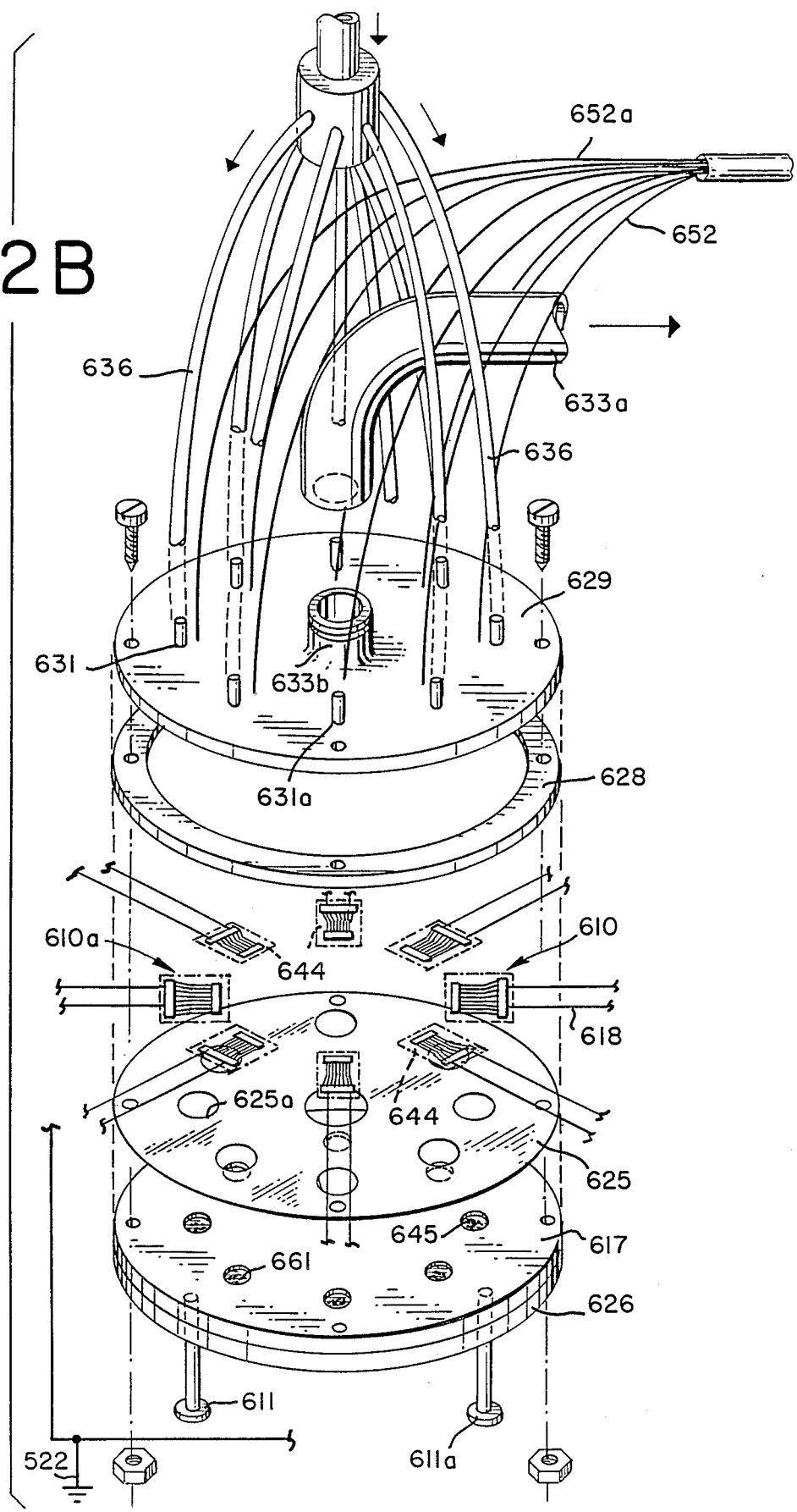

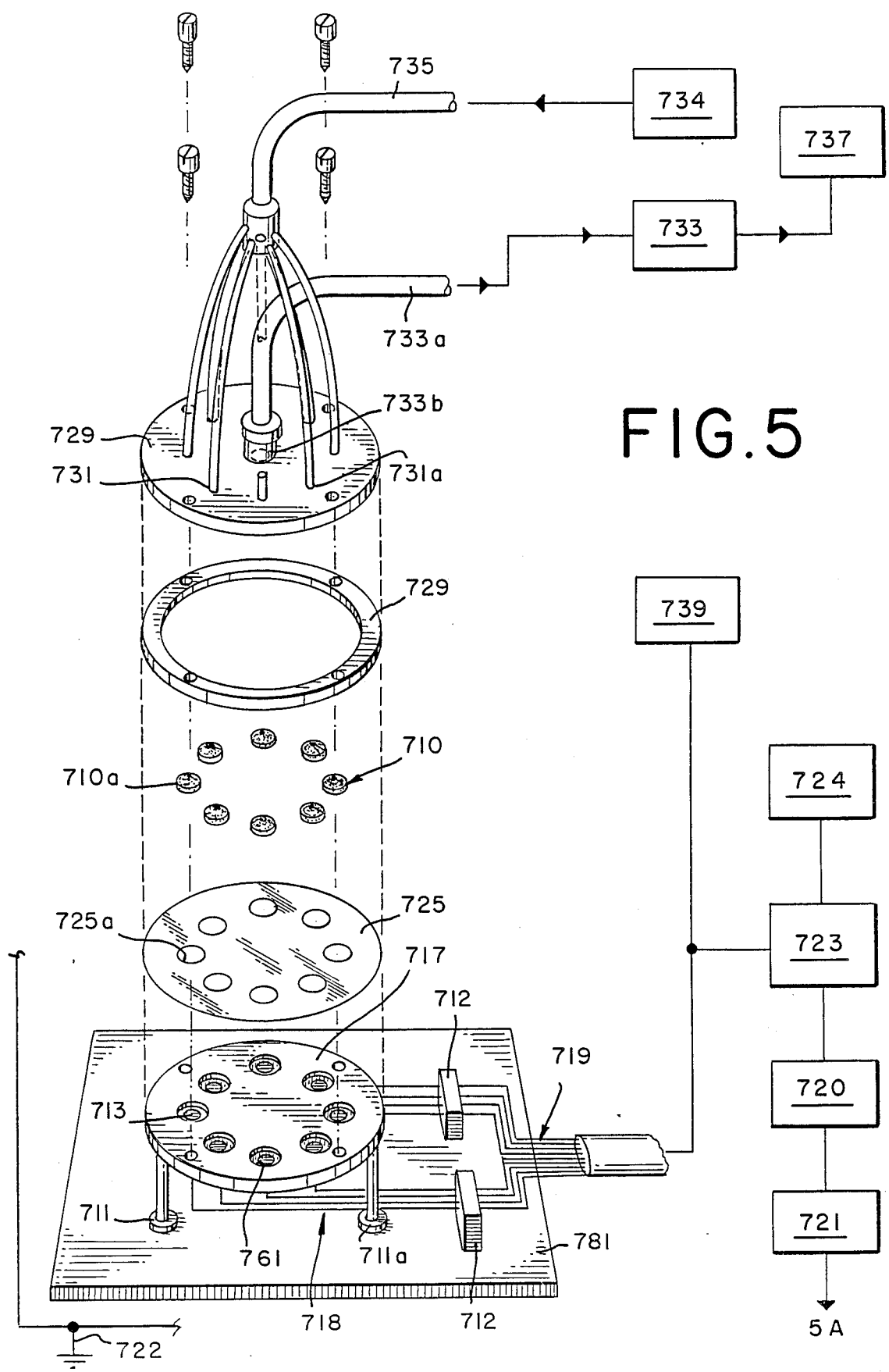

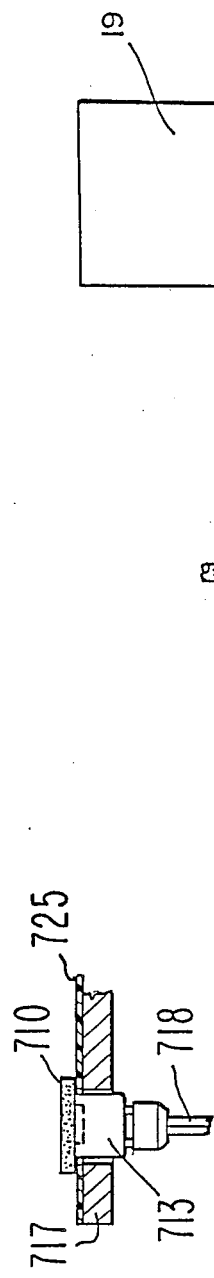
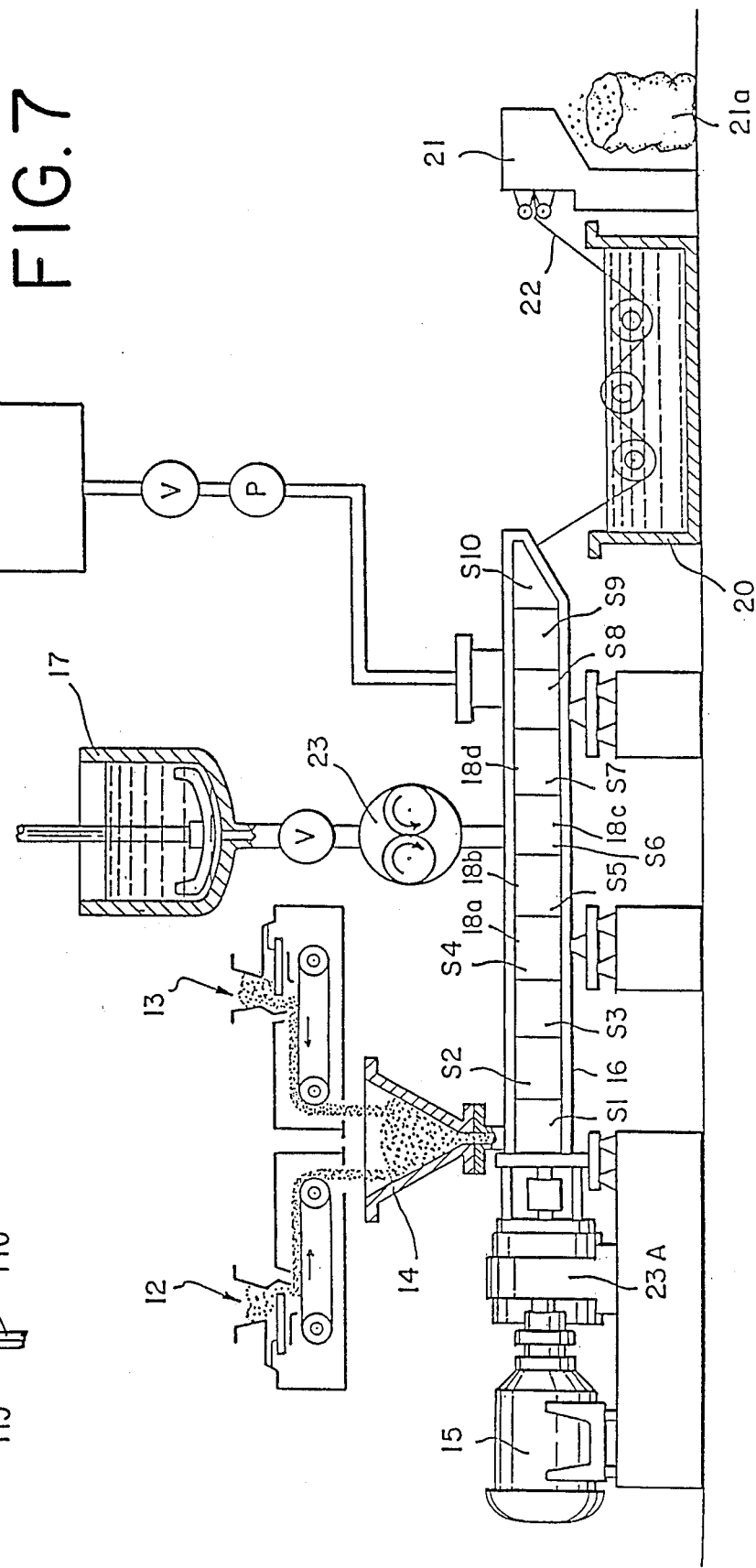

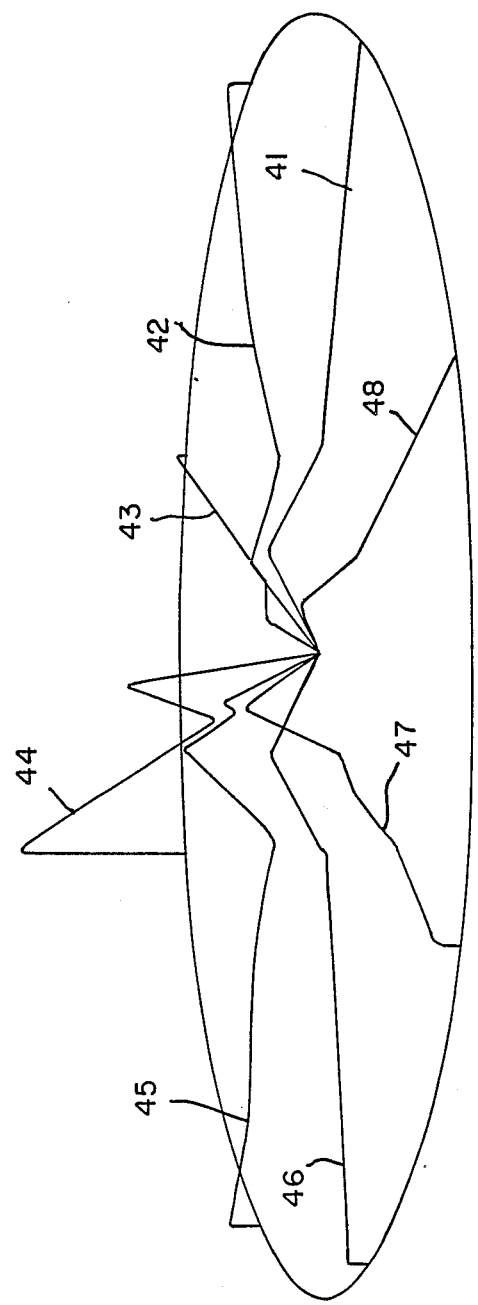
FIG.8-A

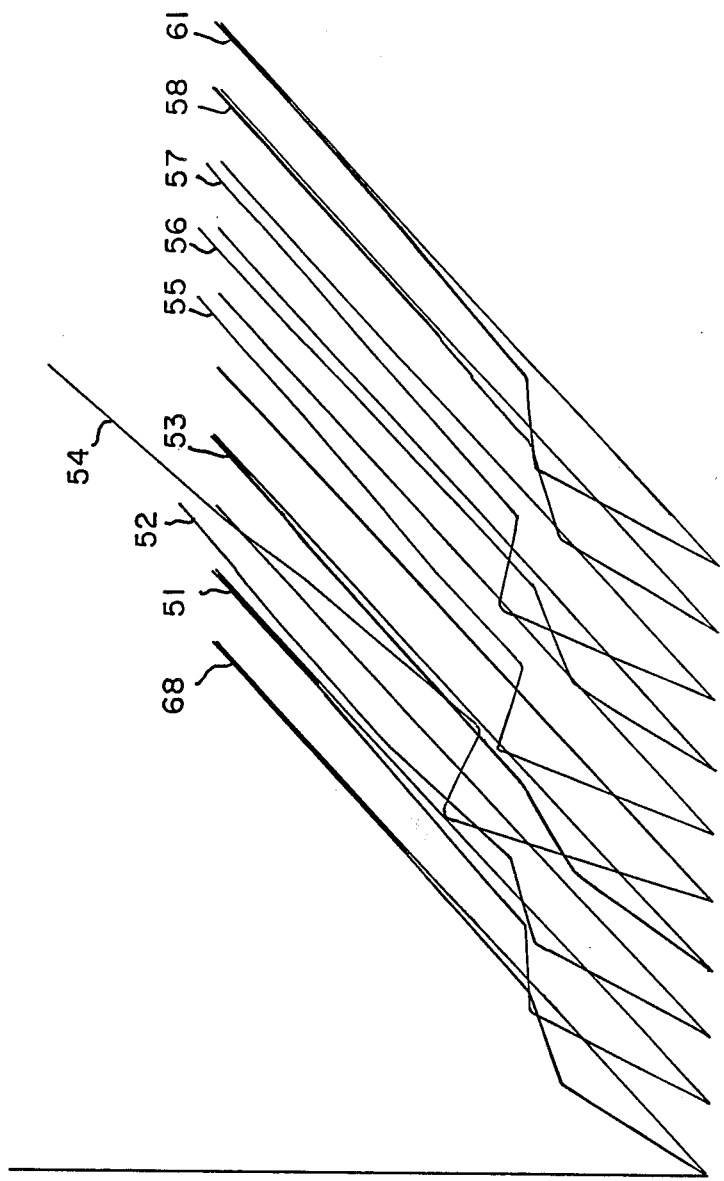

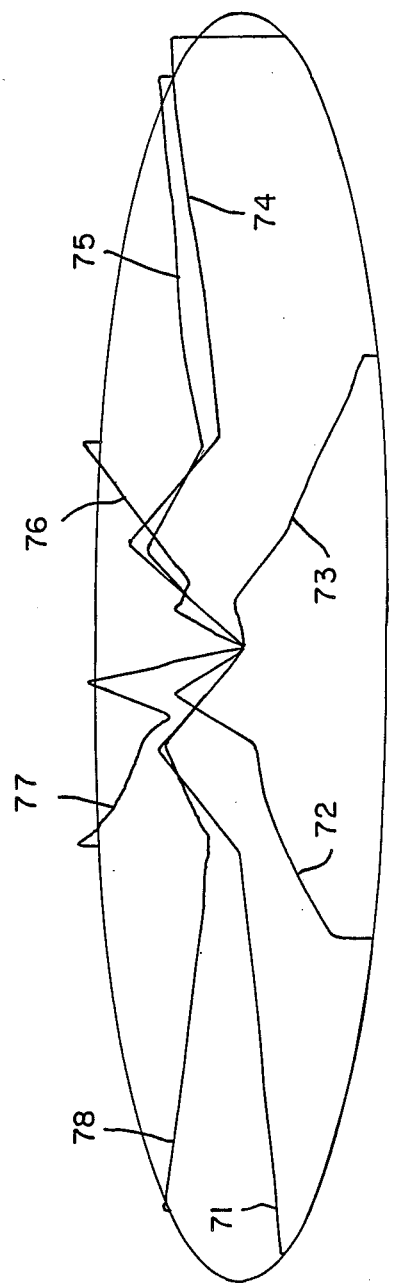
FIG. 8-C

FIG.8-D
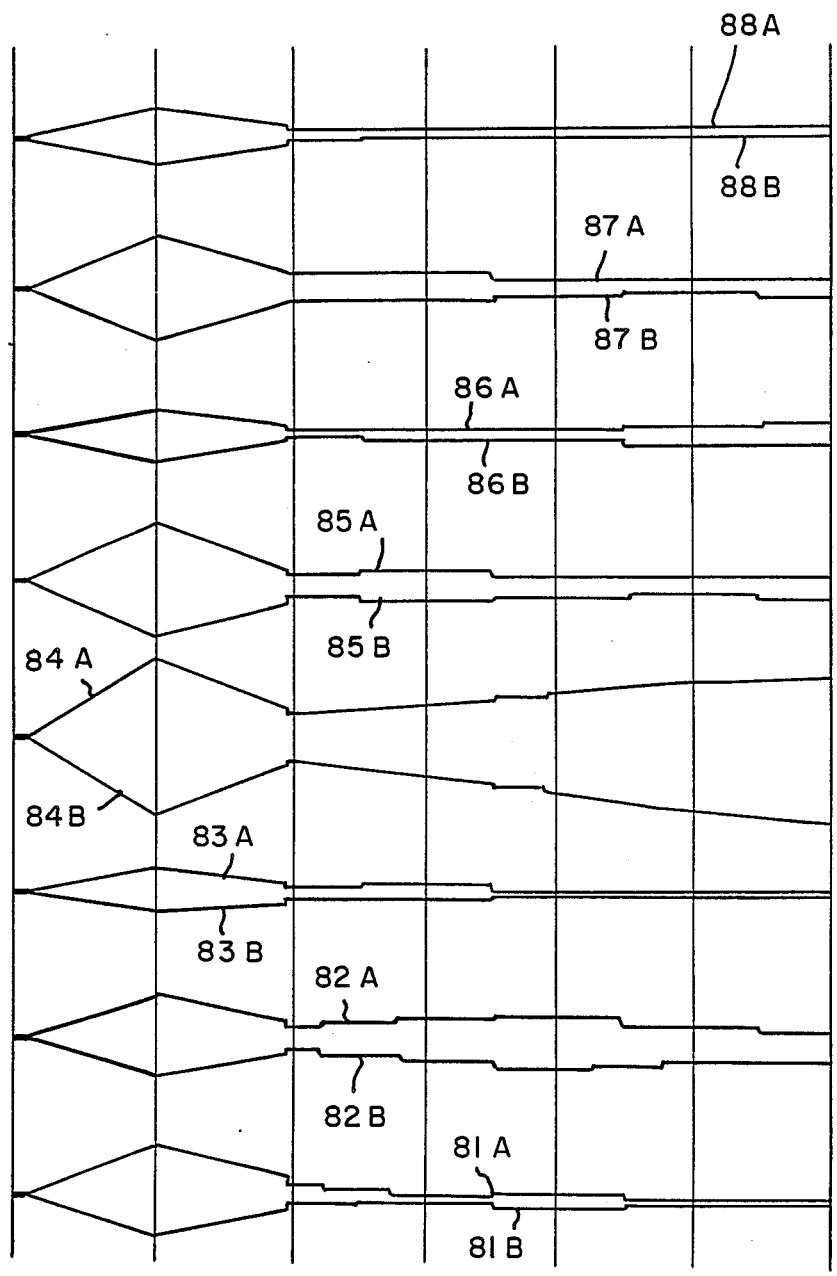

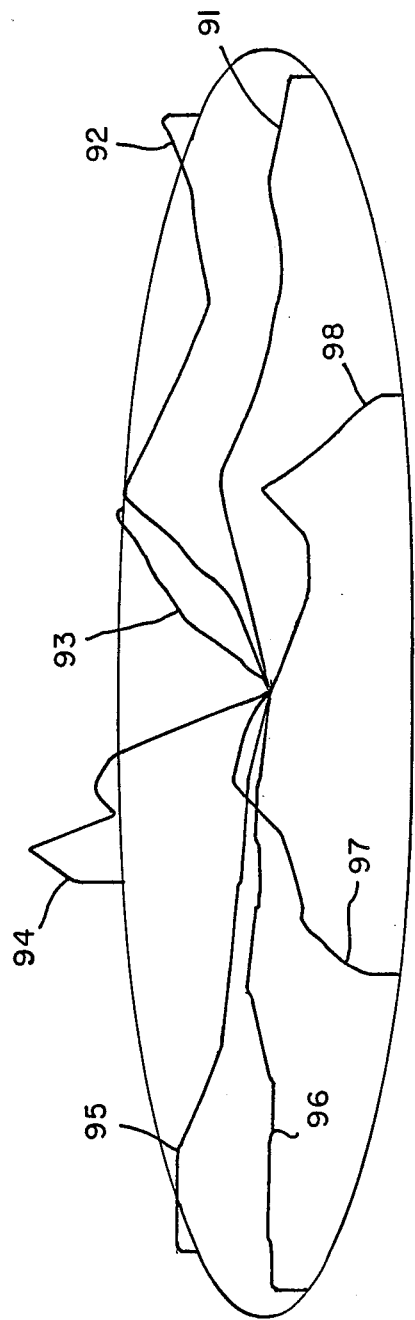
FIG.9-A

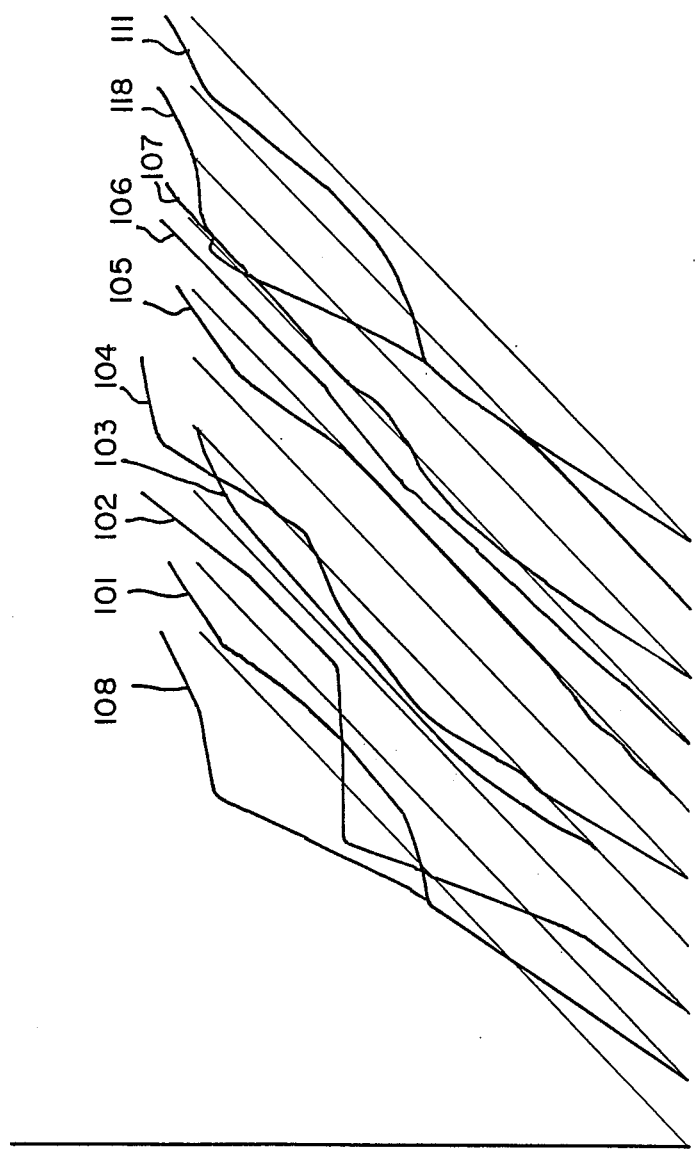

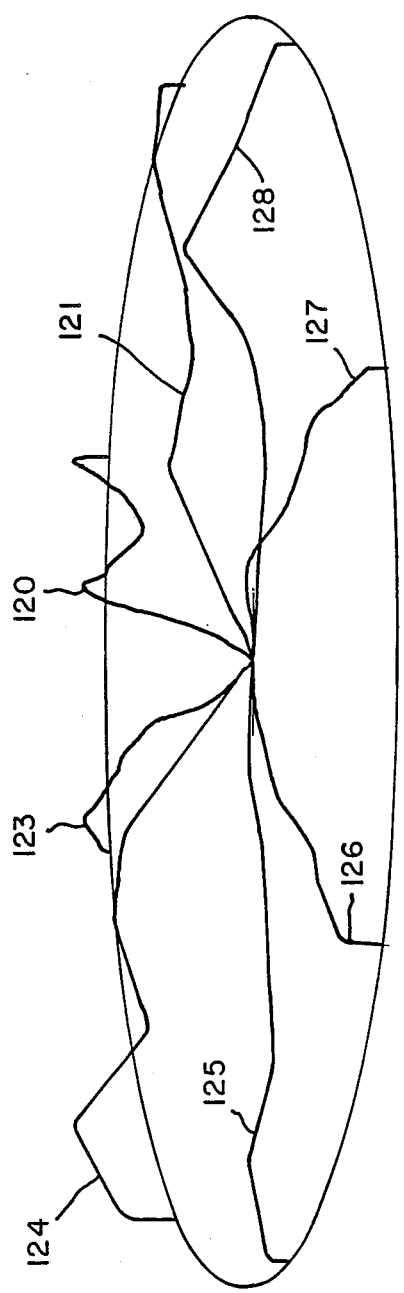
FIG. 9-C

FIG. 9-D
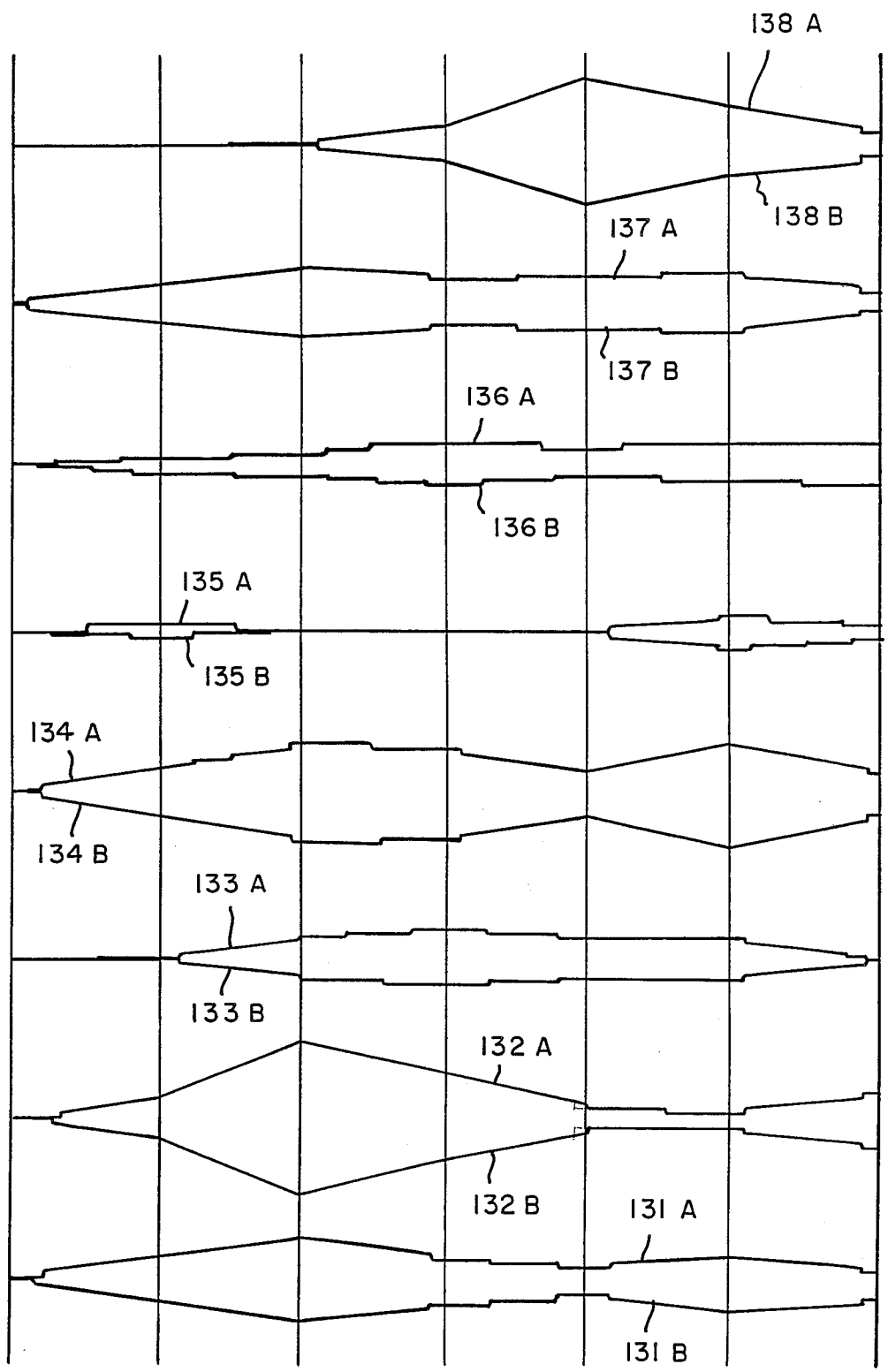

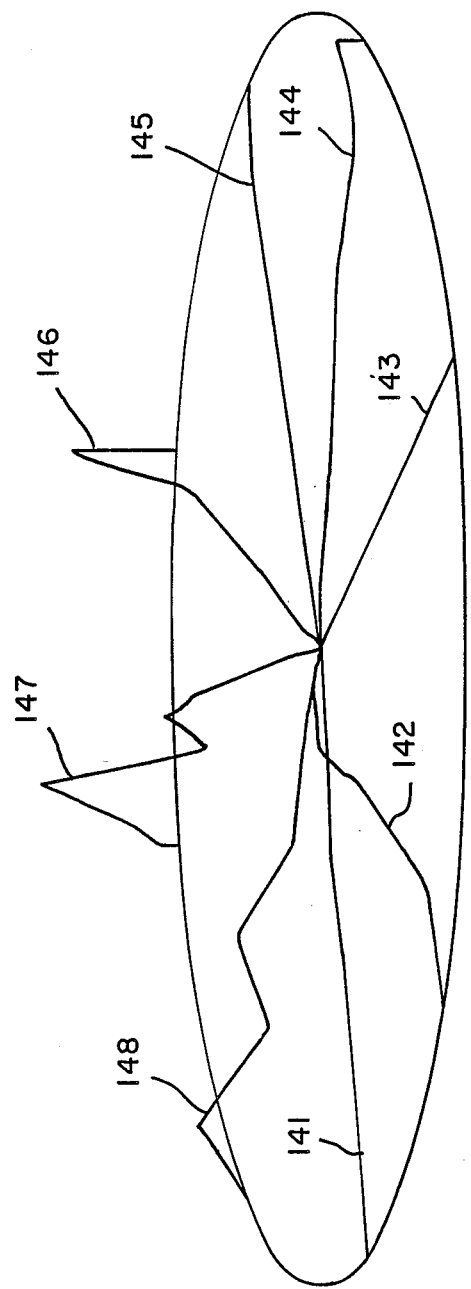
FIG.10-A

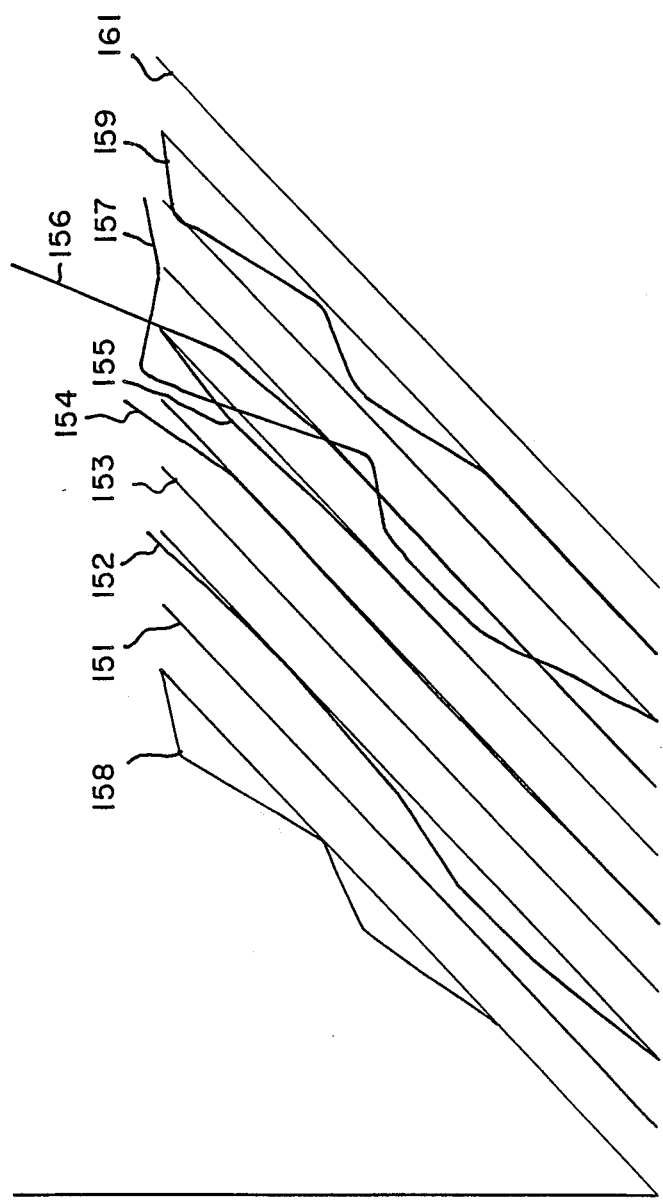
FIG.10-B

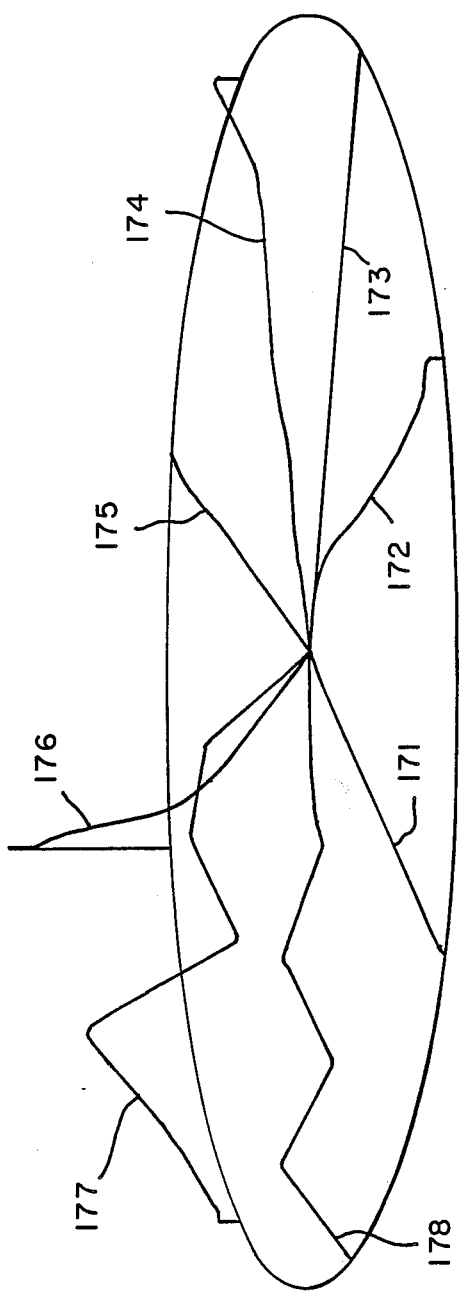
FIG.10-C

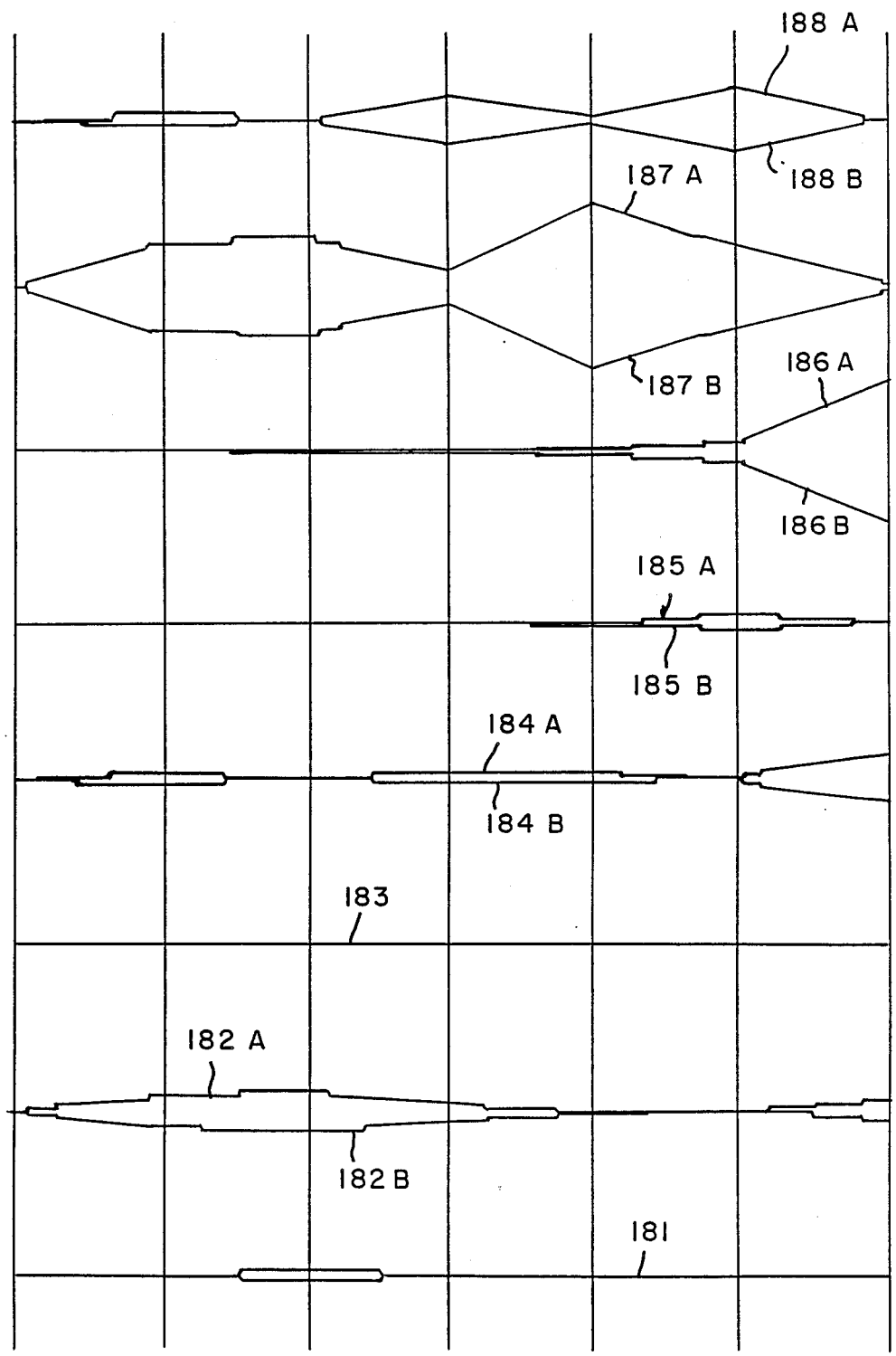
FIG.10-D

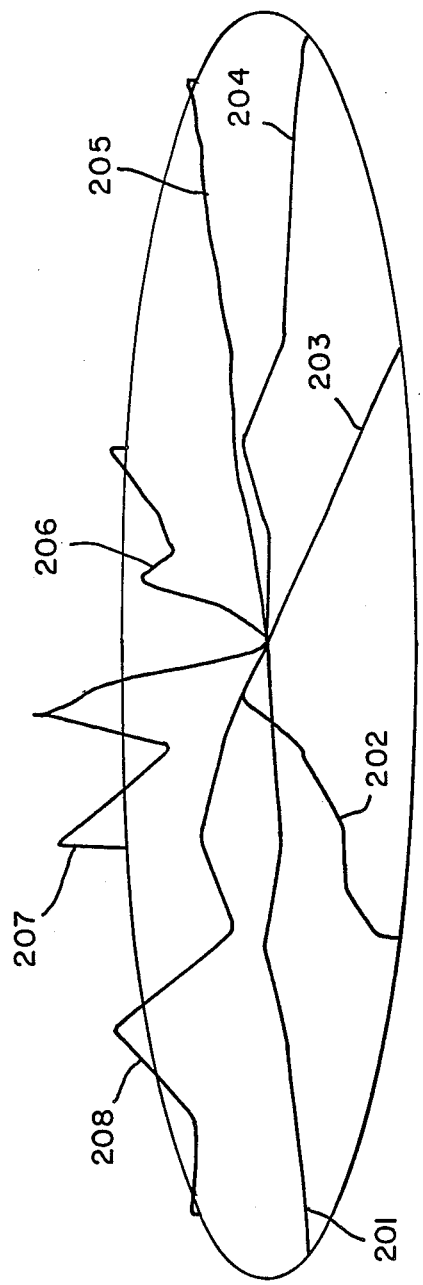
FIG.II-A

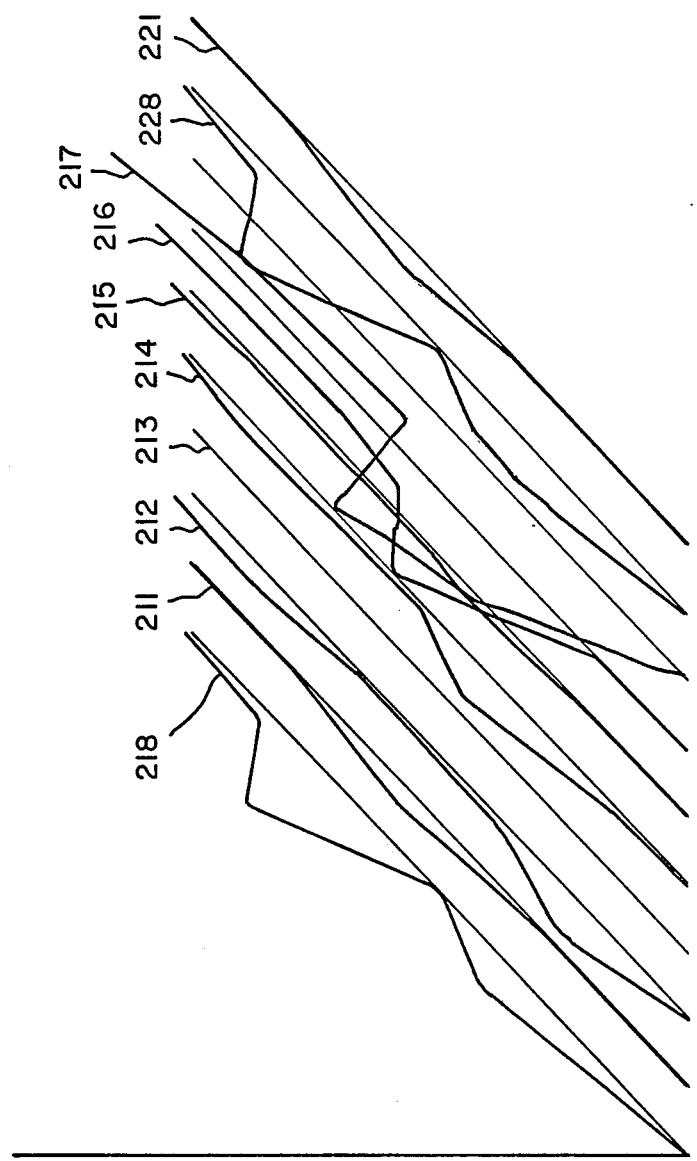

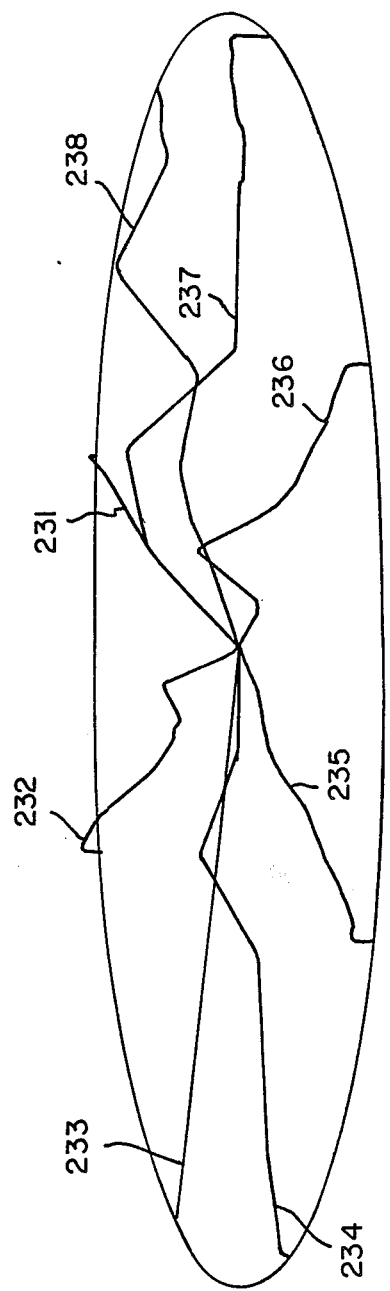
FIG.II-C

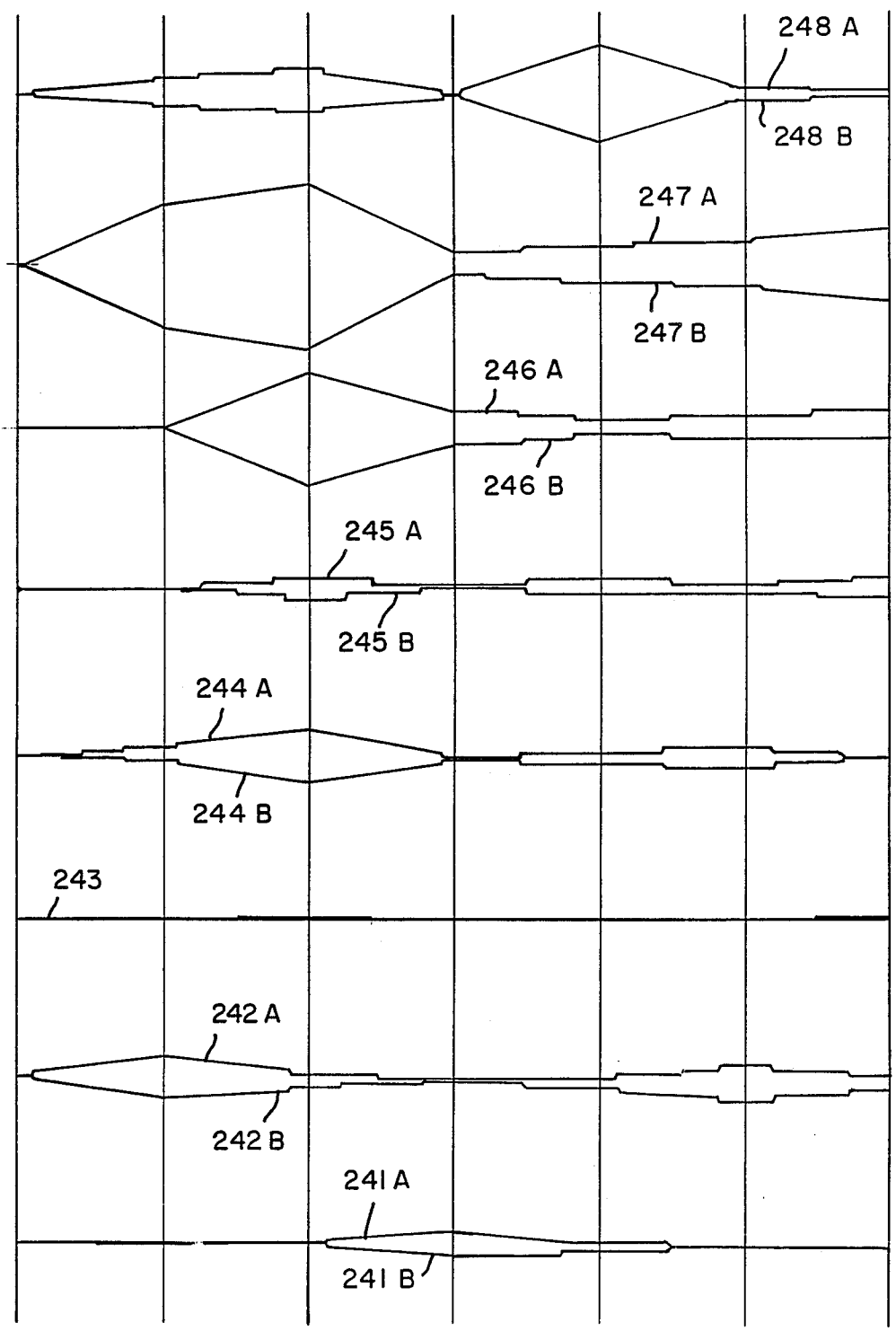
FIG.II-D

USE OF C₈-T-ALKANOLS AND C₅-C₁₁-OMEGA-ALKEN-1-OLS IN ATTRACTING INSECTS

This application is a continuation-in-part of application for U.S. Ser. No. 2,023 filed on Jan. 9, 1987, which, in turn, is a continuation-in-part of application for U.S. Ser. No. 879,426 filed on June 27, 1986, now U.S. Pat. No. 4,693,890 issued on Sept. 15, 1987.

BACKGROUND OF THE INVENTION

This invention relates to insect attractants for house flies (*Musca domestica L.* (Diptera:Muscidae)). More particularly this invention relates to compositions of matter containing C₈-t-alkanols and C₅-C₁₁-omega-alken-1-ols as attractants for *Musca domestica L.* (Diptera:Muscidae).

Fast intercontinental travel and trade are stepping up changes of importing nonindigenous inset pests into the United States. Attractants, or lures, can be of considerable aid in facilitating the early detection of such insect pests, and they are of vital importance in measuring the progress of a program aimed at eradicating a species that has become established.

In Agriculture Handbook No. 239 published by the Agricultural Research Service of the U.S. Department of Agriculture issued in June 1963 entitled, "Materials Tested As Insect Attractants", complied by M. Beroza and N. Green, n-Dodecanol is indicated to attract the Oriental Fruit Fly, the Melon Fly, the Mediterranean Fruit Fly and the Mexican Fly only slightly ("1" on a scale of 1 to 3). Decanol-1 having the structure:

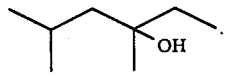

is indicated to attract the Oriental Fruit Fly at a level of "1" on a scale of 1 to 3; the Melon Fly at a level of 37 2" on a scale of 1 to 3; the Mediterranean Fruit Fly at a level of "1" on a scale of 1 to 3; and the Mexican Fruit Fly at a level of "1" on a scale of 1 to 3.

3-Ethyl-3-heptanal having the structure:

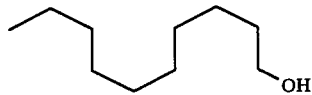

(Item No. 2826 of Beroza, et al.) is indicated to attract the Oriental Fruit Fly, the Melon Fly, the Mediterranean Fruit Fly, the Mexican Fruit Fly and the Gypsy Moth only slightly ("1" on a scale of 1 to 3).

3,5-Dimethyl-3-hexanol having the structure;

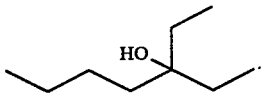

(Item No. 2843 of Beroza, et al.) is indicated to attract the Oriental Fruit Fly, the Melon Fly, the Mediterranean Fruit Fly, the Mexican Fruit Fly and the Gypsy Moth at a level of "1" on a scale of 1 to 3.

2-Methyl-2-octanol (Item No. 2886 of Beroza, et al.) is indicated to attract the Oriental Fruit Fly, the Mediterranean Fruit Fly and the Mexican Fruit Fly at a level of 37 1" on a scale of 1 to 3.

The structure of 2-methyl-2-octanol is:

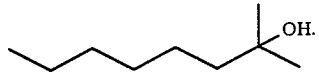

3-Methyl-3-octanol having the structure:

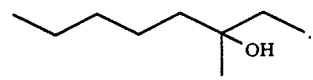

(Item No. 2889 of Beroza, et al.) is indicated to attract the Oriental Fruit Fly and the Mexican Fruit Fly at a level of "1" on a scale of 1 to 3 and is indicated to attract the Mediterranean Fruit Fly at a level of 37 2" on a scale of 1 to 3.

2,4,4-Trimethyl-2-pentanol (Item No. 2912 of Beroza, et al.) is indicated to attract the Oriental Fruit Fly, the Mediterranean Fruit Fly and the Mexican Fruit Fly at a level of "1" on a scale of 1 to 3.

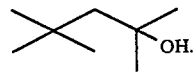

3-Ethyl-3-pentanol (Item No. 2414 of Beroza, et al.) having the structure:

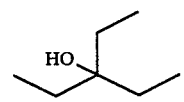

is indicated by Beroza, et al to attract the Oriental Fruit Fly, the Melon Fly, the Mediterranean Fruit Fly and the Mexican Fruit Fly at a level of "1" on a scale of 1 to 3.

Unsaturated alcohols are known with respect to controlling insects; and have been found to attract such insects. Thus, U.S. Pat. No. 4,152,422 issued on May 1, 1979 sets forth 6-nonen-1-ol in a composition of matter used as an attractant for the male Mediterranean Fruit Fly. Chem. Abstracts Volume 103, No. 71086p concerns the synthesis of (Z)-8-dodecen-1-ol and its acetate as pheromone components of the Oriental Fruit Moth (*Grapholita molesta*). This is an abstract of the article in Acta Chem. Scan. Ser. B., 1985, B39(4), pages 267-72.

U.S. Pat. No. 2,254,665 issued on Sept. 2, 1941, discloses the use of aliphatic alcohols in general in repelling insects which aliphatic alcohols have from 10 to 14 carbon atoms. Examples of the aliphatic alcohols of U.S. Pat. No. 2,254,665 are all saturated, to wit:
- dodecyl alcohol;
- octyl alcohol;
- hexadecyl alcohol;
- tetradecyl alcohol; and
- undecyl alcohol.

In "Materials Tested as Insect Attractants" compiled by M. Beroza and N. Green in Agriculture Handbook No. 239 in Table 2 it is stated that 3-methyl-1-nonen-3-ol has, on a scale of 1 to 3, an attractancy of "1" for the Oriental Fruit Fly and an attractancy of "1" for the Mediterrean Fruit Fly and 4,8-dimethyl-7-nonen-4-ol has on a scale of 1 to 3 an attractancy of 37 2" for the Oriental Fruit Fly and an attractancy of "3" for the Mediterrean Fruit Fly and an attractancy of "1" for the Mexican Fruit Fly and an attractancy of "1" for Drosophila.

Beroza, et al. also states that 3-buten-1-ol having the structure:

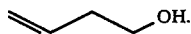

(Item No. 2762) has an attractancy of "1" for the Oriental Fruit Fly; an attractancy of "2" for the Melon Fly; an attractancy "1" for the Mediterranean Fruit Fly; an attractancy of "1" for the Mexican Fruit Fly; and an attractancy of "1" for the Gypsy Moth.

Beroza, et al. indicates for 2-methyl-3-buten-2-ol having the structure:

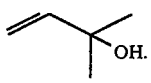

(Item No. 2941) an attractancy of "1" (on a scale 1 to 3) for:
 (i) The Oriental Fruit Fly;
 (ii) The Mediterranean Fruit;
 (iii) The Mexican Fruit Fly; and
 (iv) The Gypsy Moth.

Beroza, et al. indicates under Item No. 2965 for 10-undecen-1-ol having the structure:

(a compound of our invention) an attractancy of "1" for only the Mediterranean Fruit Fly (on a scale of 1 to 3).

Nothing in the prior art discloses the uses of $C_8$-t-alkanols and $C_5$-$C_{11}$-omega-alken-1-ols for the attractancy of *Musca domestica L.* (Diptera:Muscidae) ("house flies").

Various prior art techniques for studying feeding habits of insects have been found useful in formulating processes and apparatus for determining relative attractancy and repellency for insects. Thus, the paper "Laboratory Blood Feeding of *Culicoides Mississippiensis* (Diptera:Ceratopogonidae) Through A Reinforced Silicone Membrane" by Davis, Butler, Roberts, Reinert and Kline (J. Med. Enotomol. Vol. 20, No. 2:177–182) discloses the preparation and use of a durable silicone membrane for feeding *Culicoides Mississippiensis* in the laboratory. Further, the paper entitled "IN VITRO Feeding of Ornithodoros Ticks For Rearing And Assessment of Disease Transmission", Butler, Hess, Endris and Holscher, ACAROLOGY VI, vol. 2, published 1984 by Ellis Horwood Limited, Market Cross House, Cooper St., Chichester, West Sussex, PO 19 1EB, England discloses the advantages of feeding of haematophagous arthropods through artificial membranes. A number of preferred embodiments of our invention includes the use of the teachings of the aforementioned papers. Accordingly, the aforementioned papers are incorporated herein by reference.

BRIEF DESCRIPTION OF THE DRAWINGS

FIG. 1A is a representation of one of the landing pad sections on plate 517 of the apparatus of FIG. 1 (a transducer mechanism) where the house flies (*Musca domestica*) land if and when they are attracted by the substance being tested, e.g., 9-decen-1-ol.

FIG. 1B is a schematic diagram (blown up for illustration purposes) of an embodiment of the operational portion of the olfactometer apparatus of FIG. 1, useful in ascertaining the efficacy of the $C_8$-t-alkanols and $C_5$-$C_{11}$-omega-alken-1-ols as attractants for house flies (*Musca domestica*) but not including the utilization of the computer-assisted efficacy measuring apparatus.

FIG. 1C is a schematic diagram of the embodiment of the olfactometer apparatus of FIG. 1 (not blown up) useful in ascertaining the efficacy of the $C_8$-t-alkanols and $C_5$-$C_{11}$-omega-alken-1-ols of our invention as attractants for house flies (*Musca domestica*) indicating in schematic block flow diagram form the utilization of computer-assisted efficacy measuring apparatus.

FIG. 1F is a cut-away side elevation view of the base portion of the apparatus of FIG. 1, also illustrated in FIG. 1D, wherein the air hose 533a is connected to the remainder of the apparatus and the insects 543 have been de-anaesthetized.

FIG. 1G is a cut-away perspective view of an insect landing pad 510 as shown in FIG. 1, without any insects thereon.

FIG. 2B is a schematic diagram (exploded for illustration purposes) of the operational section of the embodiment of the olfactometer apparatus of FIG. 2A useful in ascertaining the efficacy of the $C_8$-t-alkanols and $C_5$-$C_{11}$-omega-alken-1-ols of our invention as attractants for house flies (*Musca domestica*) but not indicating the diagram of the computer-assisted efficacy measuring apparatus associated therewith as shown in FIG. 2A.

FIG. 5 is a schematic diagram (blown up for illustration purposes) of another embodiment of the olfactometer apparatus of our invention useful in ascertaining the efficacy of the $C_8$-t-alkanols and $C_5$-$C_{11}$-omega-alken-1-ols of our invention as attractants for house flies (*Musca domestica*) indicating in schematic block flow diagram form the utilization of computer-assisted efficacy measuring apparatus.

FIG. 7 is a cut-away side elevation schematic diagram of a screw extruder operating during the compounding of a polymer, (e.g., polyethylene) with one or more of the $C_8$-t-alkanols and $C_5$-$C_{11}$-omega-alken-1-ols of our invention while simultaneously adding foaming agent into the hollow portion of the barrel of the extruder and incorporates the pelletizing apparatus used in pelletizing the extruded foamed tow produced as a result of the extrusion operation.

FIG. 8A is a series of graphs depicted in three dimensions (in a circular mode for the "x" and "y" axes) showing the relative attractiveness or repellency of the $C_8$-t-alkanols and $C_5$-$C_{11}$-omega-alken-1-ol of our invention compared with a repellent, 1-nonen-3-ol, a known attractant, tagetone (0.001% in triethyl citrate) and another known attractant, "extract of used fly rearing media" (a mixture of manures, alfalfa and baking soda). The graphs are based on experiments run for a total of twenty (20) hours with six (6) intervals of 3.67 hours each. The results are tabulated in Table III, infra which list insects collected in the apparatus of FIG. 1 per interval.

FIG. 8B is a series of graphs depicted in three dimensions (in a rectangular mode for the "x" and "y" axes) showing the relative attractiveness or repellency of the $C_8$-t-alkanols and $C_5$-$C_{11}$-omega-alken-1-ols of our invention compared with a repellent, 1-nonen-3-ol, a known attractant, tagetone (0.001% in triethyl citrate) and another known attractant, "extract of used fly rearing media" (a mixture of manures, alfalfa and baking soda). The graphs are based on experiments run for a total of twenty (20) hours with six intervals of 3.67 hours each. The results are the same as those for FIG. 8A and are tabulated in Table III, infra.

FIG. 8C depicts a replicate of the data summarized in the series of graphs setting forth data of Table III (depicted in FIG. 8A).

FIG. 8D is the series of graphs of FIGS. 8A and 8C taken together and depicted in two dimensions.

FIG. 9A is a series of graphs depicted in three dimensions (in a circular mode for the "x" and "y" axes) showing the relative attractiveness or repellency of the $C_8$-t-alkanols and $C_5$-$C_{11}$-omega-alken-1-ols of our invention compared with a repellent, 1-nonen-3-ol a known attractant, tagetone (0.001% in triethyl citrate and another known attractant, "extract of used fly rearing media" (mixtures of manures, alfalfa and baking soda). The graphs are based on experiments run for a total of one hour with six intervals of 10 minutes each. The results are tabulated in Table IV, infra.

FIG. 9B is a series of graphs depicted in three dimensions (in a rectangular mode for the "x" and "y" axes) showing the relative attractiveness or repellency of the $C_8$-t-alkanols and $C_5$-$C_{11}$-omega-alken-1-ols of our invention compared with a repellent, 1-nonen-3-ol, a known attractant, tagetone (0.001% in triethyl citrate) and another known attractant, "extract of used fly rearing media" (mixture of manures, alfalfa and baking soda). The graphs are based on experiments run for a total of one hour with six intervals of ten minutes each. The results are the same as the results set forth in the graphs of FIG. 9A.

FIG. 9C depicts a replicate of the data in a series of graphs in three dimensions (in a circular mode for the "x" and "y" axes) of FIG. 9A.

FIG. 9D is a series of graphs of FIGS. 9A and 9C taken together and depicted in two dimensions.

FIG. 10A is a series of graphs depicted in three dimensions (in a circular mode for the "x" and "y" axes) showing the relative attractiveness or repellency of the C8-t-alkanols and C5–C11-omega-alken-1-ols of our invention compared with a repellent, 1-nonen-3-ol, a known attractant, tagetone (0.001% in triethyl citrate) and another known attractant "extract of used fly rearing media" (a mixture of manures, alfalfa and baking soda). The graphs are based on experiments run for a total of two (2) hours with six (6) intervals of 20 minutes each. The results are tabulated in Table V, infra.

FIG. 10B is a series of graphs depicted in three dimensions (in a rectangular mode for the "x" and "y" axes) showing the relative attractiveness or repellency of the C8-t-alkanols and C5–C11-omega-alken-1-ols of our invention compared with a repellent, 1-nonen-3-ol, a known attractant, tagetone (0.001% in triethyl citrate) and another known attractant, "extract of used fly rearing media" (a mixture of manures, alfalfa and baking soda). The graphs are based on experiments run for a total of two (2) hours with separate 20 minute intervals. The results are tabulated in Table V, infra.

FIG. 10C depicts a replicate of the data set forth in the graphs of FIG. 10A.

FIG. 10D is a series of graphs setting forth the data of FIGS. 10A and 10C depicted in two dimensions.

FIG. 11A is a series of graphs depicted in three dimensions (in a circular mode for the "x" and "y" axes) showing the relative attractiveness or repellency of the C8-t-alkanols and C5–C11-omega-alken-1-ols of our invention compared with a repellent, 1-nonen-3-ol, a known attractant, tagetone (0.001% in triethyl citrate) and another known attractant, "extract of used fly rearing media" (a mixture of manures, alfalfa and baking soda). The graphs are based on experiments run for a total of six hours with six (6) intervals of one hour each. The results are tabulated in Table VI, infra.

FIG. 11B is a series of graphs depicted in three dimensions (in a rectangular mode for the "x" and "y" axes) showing the relative attractiveness or repellency of the C8-t-alkanols and C5–C11-omega-alken-1-ols of our invention compared with a repellent, 1-nonen-3-ol, a known attractant, tagetone (0.001% in triethyl citrate) and another known attractant, "extract of used fly rearing media" (mixture of manures, alfalfa and baking soda). The graphs are based on experiments run for a total of six hours with six (6) intervals of one hour each. The results are tabulated in Table VI, infra and are the same as depicted in FIG. 11A.

FIG. 11C depicts in graphical form a replicate of the data set forth in graphical form in FIG. 11A.

FIG. 11D is a series of graphs depicting the data set forth in graphical form in FIGS. 11A and 11C, depicted in two dimensions.

SUMMARY OF THE INVENTION

Figure 1:
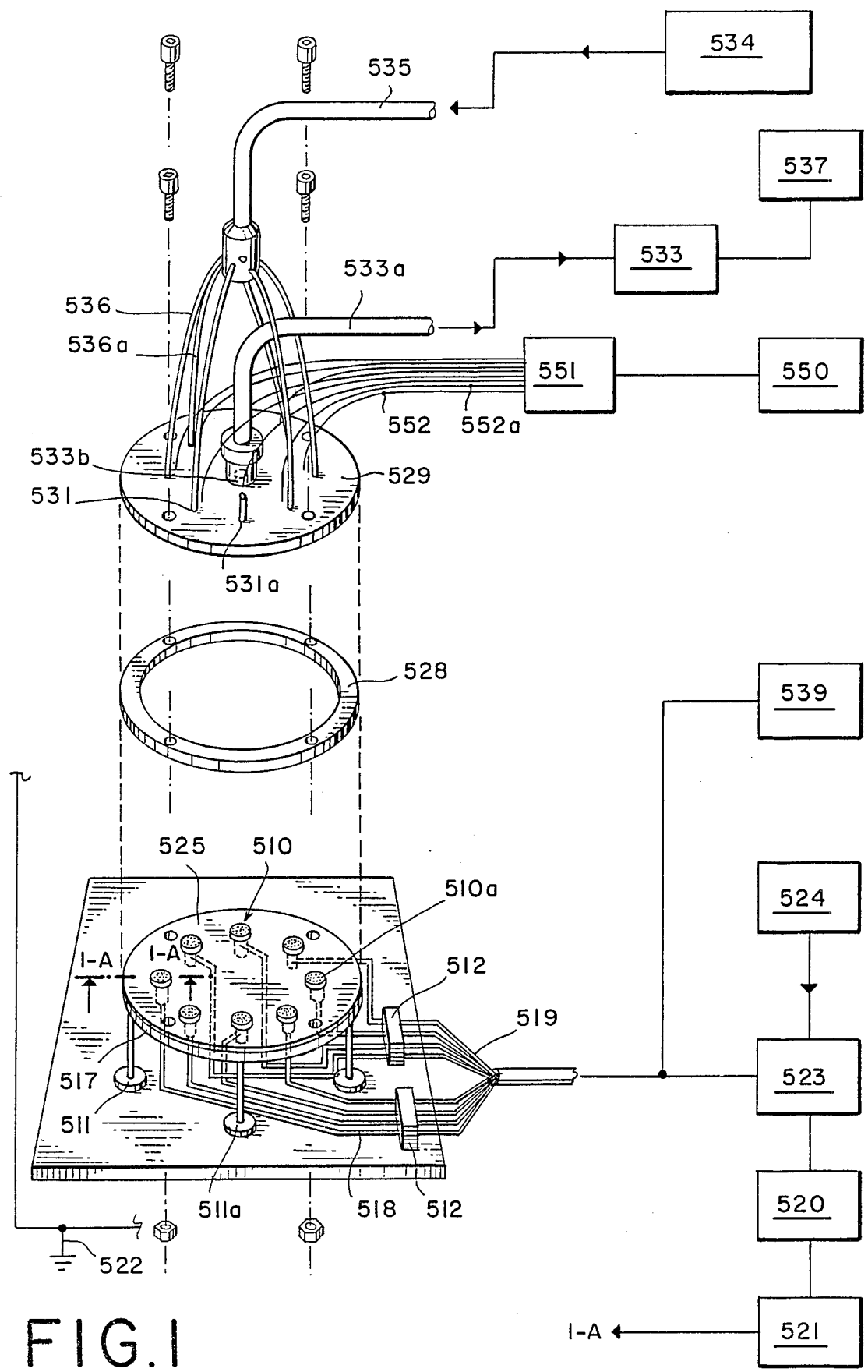
FIG. 1 is a schematic diagram (blown up for illustration purposes) of an embodiment of the olfactometer apparatus useful, inter alia, in ascertaining the efficacy of the $C_8$-t-alkanols and $C_5$-$C_{11}$-omega-alken-1-ols as attractants for house flies (*Musca domestica*) indicating in schematic block flow diagram form the utilization of computer-assisted efficacy measuring apparatus.

Our invention relates to the use of C8-t-alkanols and C5–C11-omega-alken-1-ols as attractants for house flies (*Musca domestica L.* (Diptera:Muscidae)). Our invention also is intended to encompass insect traps and trapping compositions containg such C8-t-alkanols and C5–C11-omega-alken-1-ols. Trapping systems so employed are, for example, standard ZOECON ® sticky traps consisting of a ZOECON PHEROCON ® 1C trap with a 2 cm×2 cm strip of formulated slow release attractant (one or more of the C8-t-alkanols and C5–C11-omega-alken-1-ols of our invention) suspended inside the trap.

Examples of C8-t-alkanols and C5–C11-omega-alken-1-ols useful in the pracatiace of our invention are as follows:

(i) 9-decen-2-ol having the structure:

(ii) 10-undecen-1-ol having the structure:

(iii) 3-ethyl-3-hexanol having the structure:

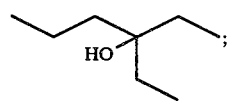

(iv) 3-ethyl-2-methyl-3-pentanol having the structure:

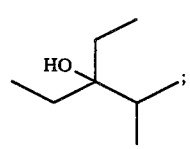

(v) 2,3-dimethyl-3-hexanol having the structure:

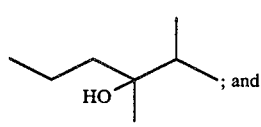

(vi) 3-methyl-3-buten-2-ol having the structure:

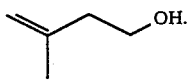

The foregoing $C_8$-t-alkanols and $C_5$-$C_{11}$-omega-alken-1-ols of our invention are also useful in insect traps applied to trapping *Musca domestica L.* (Diptera:-Muscidae) as described in Kydonieus & Beroza "Insect Suppression & Controlled Release Pheremone Systems" published by the CRC Press Inc., 1982, at Volume I, pages 6–8 (Chapter I) and Volume II, §3, at pages 3–65.

The Kydonieus & Beroza reference is incorporated herein by reference.

Testing Methodology

An apparatus for testing insect repellency and attractancy of $C_8$-t-alkanols and $C_5$-$C_{11}$-omega-alken-1-ols of our invention comprises:

(i) active and passive insect interest electronic measuring and recording means connected to an electric power supply source;

(ii) enclosed insect feeding means having controlled limited access to the external environment surrounding said apparatus and associated with said measuring and recording means, said insect feeding being located at a fixed insect feeding means location defined according to x, y and z coordinates in a defined first 3-space, said insect feeding means consisting essentially of:
  (a) an insect feeding surface comprising at least two-spaced electrically conductive elements:
    (1) connected to said measuring and recording means; and
    (2) forming a complete circuit, said elements having such dimensions and spacing from one another as to cause an attracted insect to complete a circuit of electron flow through or proximately to said elements;
  (b) immediately beneath said insect feeding surface a composition of matter comprising the molecules to be tested for attractancy and repellency;
  (c) immediately beneath said molecules to be tested, a feeding stimulant composition or a stimulant composition for said insects;

(iii) optionally, steady state direct lighting means for supplying a beam of direct light having a given substantially constant intensity or intensities and wavelength or wavelengths to said feeding and/or stimulating means location; and (iv) steady state air supply, air conduction and air removal means for supplying, conducting and removing air at a substantially constant mass flow rate and substantially constant linear velocity to, past and from a second 3-space immediately above said insect feeding and/or stimulating surface (and, in the event that a steady-state direct lighting means is used, simultaneously with the supplying of said beam of direct light to said feeding and/or stimulating means location) substantially immediately above said insect feeding and/or stimulating surface, said insect feeding and/or stimulating surface structure being constructed so that said measuring and recording means is sensitive to the completion of a circuit of electron flow through or proximate said conductive elements of said insect feeding and/or stimulating surface, whereby the number and frequency of the insects attracted to the proximity of said feeding and/or stimulating means is capable of being determined either (a) using said measuring and recording means or (b) visually.

The apparatus used in testing the efficacy of the $C_8$-t-alkanols and $C_5$-$C_{11}$-omega-alken-1-ols of our invention may be juxtaposed in an upright position as set forth in FIGS. 1–3 and 5 described in detail, infra, or it may be juxtaposed in an inverted or substantially inverted position; or it may be juxtaposed in a sagital position (not shown in drawings).

Thus, the process for testing insect repellency and attractancy of molecules using such apparatus as set forth, supra, first provides such apparatus and then comprises:

(i) anaesthetizing selected insects at a location apart from the feeding means in the apparatus;

(ii) then supplying one or more anaesthitized insects to said first defined 3-space in the apparatus;

(iii) then enclosing said first 3-space surrounding said feeding means whereby access thereto is limited to the air supply, air conduction and air removal means of the apparatus;

(iv) then forming an electrical circuit connection between said measuring and recording means and said feeding means;

(v) then supplying, conducting and removing air at a substantially constant mass flow rate and substantially constant linear velocity to, past and from said second defined 3-space; then (vi) (optionally) simultaneously supplying direct light to said second defined 3-space, the optional supplying of light and the supplying of air being carried out at such conditions and for such a period of time that the anaesthetized insects are de-anaesthetized and recommence life activities; and (vii) then observing on said measuring and recording means the number and frequency of de-anaesthetized insects attracted to the surface or proximity of said feeding means.

A second testing technique concerns the electrophysiological study of the neural corrolates of attraction and repulsion in *Musca domestica L.* (Diptera:Muscidae)(house flies). Different points in the house fly olfactory neuroarchitecture were studied using electrophysiology in an effort to identify the neural corrolates of attractant and repellent signals resulting from potentially attractant and repellent substances.

Recordings from the antennal lobe of the deuterocerebrum of the *Musca domestica L.* (Diptera:-Muscidae) showed that the repellent signals were highly distinguishable from the attractant signals. Signals from repellents showed a shift in base line potential of approximately 25 m Volts whereas attractant signals (e.g., in the case of 2,3-dimethyl-3-hexanol) showed no shift, Thus, neural signals of the antennal lobe are used herein as an assay for olfactory canvassing to predict behavioral activity of the *Musca domestica L.* (Diptera:-Muscidae) (house fly).

Controlled Release Application

Our invention also relates to the formation of insect attractant-containing polymeric pellets by means of introduction into a single screw or twin screw extruder of, in series, thermoplastic polymer followed by insect attractant which is compatible with the thermoplastic polymer, in turn, followed by introduction of a gaseous blowing agent or blowing agent which will produce a gas which is inert to the polymer and to the insect attractant, e.g., one or more $C_8$-t-alkanols and $C_5$-$C_{11}$-omega-alken-1-ols of our invention or combination thereof.

In the alternative, the use of the foaming agent can be omitted.

The nature of the extruder utilized in this aspect of our invention to form the polymeric insect attractant particles of our invention may be either single screw or double screw. Thus, the types of extruder that can be used are disclosed at pages 246–267 and 332–349 of the Modern Plastics Encyclopedia, 1982–1983 published by the McGraw-Hill Publishing Company, the disclosure of which is incorporated by reference herein. More specifically, examples of extruders which are useable in carrying out this aspect of our invention (with modification for introduction of insect attractant downstream from introduction of the polymer and optionally with a further modification that the gaseous blowing agent is introduced still further downstream from the point of introduction of insect attractant) are as follows:

1. The Welex "Super Twinch" 3.5"extruder manufactured by Welex Incorporated, 850 Jolly Rd., Blue Bell, Pa. 19422;
2. Krauss-Maffei twin screw extruder manufactured by the Krauss-Maffei Corporation/Extruder Division, 3629 West 30th St. South, Wichita, Kans. 67277;
3. Modified- Sterling Model 4000 and 5000 series extruder manufactured by Sterling Extruder Corporation of 901 Durham Ave., South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Rte. 206 South, Somerville, N.J. 08876;
6. The ZSK Twin Screw Co-Rotating Extruder manufactured by the Werner & Pfleiderer Corporation of 663 East Crescent Ave., Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff Single Screw, Twin Screw, or Foam Extrusion Equipment manufactured by Berstorff Corporation, P.0. Box 240357, 8200-A Arrowridge Boulevard, Charlotte, N.C. 28224.

In producing the insect attractant-containing polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene vinyl acetate with about 9 to 60% vinyl acetate and ethylene/ethyl acrylate with about 6 to 18% ethyl acrylate.

Resins of the type disclosed for use as co-polymers are comercially available in the molding powder form. For example, ethylene vinyl acetate co-polymers are marketed by the E. I. duPont de Nemours Company under the tradename "ELVAX®" and by the Arco Polymer Division under the trademark "DYLAND®" and by the Exxon Corporation of Linden, N.J. under the trademark "DEXXON®". Ethylene/ethyl acrylate co-polymers are marketed by Union Carbide Corporation under the tradename "EEA RESINS".

The polymer is added to the single screw or twin screw extruder at a feed rate in the range of from about 80 up to about 300 pounds per hour while maintaining the temperature in the screw extruder between about 160° and about 240° C. If the polymer or co-polymer powder is added to the extruder at a reference "barrel segment", then the insect attractant is added to the extruder under pressure downstream from the addition point of the polymer at 1 or more "barrel segments" S-2, S-3, S-4, S-5, S-6, S-7, S-8 or S-9.

Thus, the invention provides a process for forming insect attractant-containing polymeric particles such as polymeric pellets which include a relatively high concentration of insect attractants. The insect attractant added at "barrel segments" "S-2, S-3, S-4, S-5, S-6, S-7, S-8 or S-9" of the single screw or twin screw extruder is to be compatible with the polymer added at "barrel segment" S-1 of the single screw or twin screw extruder.

The proportion of insect attractant is limited only by either (a) its solubility in the resin or mixture of resins used and/or (b) the volume ratio of microvoids in the polymer to said polymer and/or (c) the solubility of the insect attractant in the polymer on solidification. The proportion of insect attractant can in many instances go up to 45% by weight or even higher.

Thus, the proportion of insect attractant to resin can vary from small but effective amounts on the order of about 1% of the weight of the resin body up to about 45% by weight of the resin body. In general, it is preferred to use between about 5% up to about 30% based on the weight of resin body of the insect attractant. This is an optimum amount balancing the proportion of insect attractant against the time period over which the article emits the insect attractant and against the tendency of the insect attractant to "oil out". This "oiling out" is specifically avoided as a result of the use of foaming agent.

As stated, supra, various polymers are useful in the practice of our invention. Specific examples of polymers useful in the practice of our invention are as follows:

(a) DYLAN ® brand of low density polyethylene DYLAN ® is a trademark owned by the Atlantic Richfield Company of Los Angeles, Calif.;
(b) DYLITE ® of expandable polystryene compositions. DYLITE ® is a trademark of the Atlantic Richfield Company of Los Angeles, Calif.;
(c) SUPER DYLAN ® a high density polyethylene. SUPER DYLAN ® is a trademark of the Atlantic Richfield Company of Los Angeles, Calif.;
(d) Blended polyethylene and carbon black as specifically taught in U.S. Pat. No. 4,369,267 issued on Jan. 18, 1983, the specification for which is incorporated by reference herein;
(e) Polystyrene as disclosed in U.S. Pat. No. 4,369,227 issued on Jan. 18, 1983, the specification for which is incorporated herein;
(f) Polyene/alpha-olefin as exemplified and disclosed in U.S. Pat. No. 4,369,291, the specification for which is incorporated by reference herein;

(g) Poly-alpha-olefins as exemplified in Canadian Letters Pat. No. 1,137,069 issued on Dec. 7, 1982, the specification for which is incorporated herein;

(h) Polymeric compositions as disclosed in Canadian Letters Pat. No. 1,137,068 issued on Dec. 7, 1982, the specification for which is incorporated by reference herein;

(i) Poly-alpha-olefins disclosed in Canadian Letters Pat. No. 1,137,067, the specification for which is incorporated by reference herein;

(j) Polyolefins described in Canadian Letters Pat. No. 1,137,066, the specification for which is incorporated by reference herein;

(k) Polyethylene oxides as disclosed in Canadian Letters Pat. No. 1,137,065 issued on Dec. 7, 1982, the specification for which is incorporated by reference herein;

(l) Olefin polymers and co-polymers as disclosed in Canadian Letters Pat. No. 1,139,737, the disclosure of which is incorporated by reference herein. Canadian Patent No. 1,139,737 was issued on Jan. 18, 1983;

(m) Polyolefins disclosed in Canadian Letters Pat. No. 1,139,738, the disclosure of which is incorporated by reference herein. Canadian Pat. No. 1,139,738 was issued on Jan. 18, 1983;

(n) Chlorinated PVC as disclosed in *Polymer* 1982, 23 (7, Suppl.), 1051-6 abstracted at Chem. Abstracts 97:145570y, 1982;

(o) Polyepsilon caprolactone co-polymers made by means of alcohol initiated polymerization as disclosed in *J. Polym. Sci.* Polym. Chem. Ed. 1982, 20(2), pages 319–26, abstracted at Chem.Abstracts, Volume 96:123625x, 1982;

(p) Styrene acrylonitrile co-polymers as disclosed in Diss. Abstracts, Int. B, 1982, 42(8), 3346 and abstracted at Chem. Abstracts 96:143750n (1982);

(q) Co-polymers of epsilon caprolactone with 1,4-butane diol as disclosed at Kauch. Rezine, 1982, (2), 8–9, abstracted at Chem. Abstracts, Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al, *J. Polym. Sci.* Polym. Phys. Ed. 1982, 20(2), 191-203;

(t) Plasticized polyepsilon caprolactone co-polymers containing dimethyl phthalate plasticizers as set forth in Japanese Pat. No. J81/147844, abstracted at Chem. Abstracts, Volume 96:69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Optionally, downstream from the addition point of the insect attractant a gaseous or liquid containing blowing agent may be added (e.g., at barrel segments S-5, S-6, S-7, S-8 or S-9 and S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed insect attractant-containing polymer particle.

The feed rate range of insect attractant may be between about 0.5% up to about 45% by weight of the polymer.

The die of the extruder may create rod, sheet, film or ribbon. The resulting product may then, if desired, be pelletized to form foamed insect attractant-containing polymer particles or the ribbon may be used "as-is" as an insect attractant-containing polymeric article of manufacture itself.

In addition to the optional gaseous blowing agents (which are necessarily "inert" gases), blowing agents may be added at some point on the extruder which will create gaseous voids in the insect attractant-containing polymeric articles of our invention and these "blowing agents" are well known to one having ordinary skill in the art. Examples of such non-gaseous containing materials which yield gases on admixture with the polymer in the extruder but which are still inert to the insect attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1-5, the specification for which is incorporated by reference herein;

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference; and (iv) Azo bis(formamide); diazoaminobenzene; N,N'-dinitrosopentamethylene tetramine; N,N'-dimethyl-N,N'-dinitrosoterephthalamide; p,p'-oxy-bis(benzene sulfonyl semicarbazide); azo bis(isobutyronitrile); p,p'-oxy-bis(benzene sulfonyl hydrazide); p,p'-diphenyl-bis(sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

FIG. 1 is an exploded view of a first embodiment of the olfactometer apparatus used in testing the efficacy of, $C_8$-t-alkanols and $C_5$-$C_{11}$-omega-alken-1-ols as house fly attracting materials. Air source 534 feeds air through line 535 through air distributors 536, 536a et seq. onto base plate 517 containing insect landing sites 510, 510a, et seq. The base plate 517 is separated from the spacer plate 529 for the air lines 536 whereby the air lines 536 are held in place at positions 531, 531a et seq. using spacer ring 528. Air exits through line 533a using exhaust fan 533.

Simultaneously with the supplying of air from air source 534, light is supplied through light guides 552, 552a et seq. from light source 551 which is powered by electric power supply 550. An example of such light guide is marketed by RADIO SHACK ® Division of Tandy Corporation of Fort Worth, Tex. 76102 under the trademark ARCHER ® Catalog No. 276–228 ("1.0 mm optical plastic fiber length 5 meters"). An example of light source 551 is KRATOS Monochromatic Illuminator GM 100 Miniture VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator. The base plate 517 is also separated from the spacer plate 529 for the light guides 552 whereby the light guides 552, 552a et seq. are held in place also at positions 531, 531a et seq. In the first embodiment illustrated in FIG. 1 as well as in FIGS. 1B, 1C, 1D and 1F, spacer ring 528 separates plate 529 which holds the air line 536 and the light guide 552 in place from plate 517 on which landing pads 510 are located.

The olfactometer of FIG. 1 is assisted with computer apparatus shown in schematic form and block flow diagram form using reference numerals 520, 521, 523, 524 and 539. Dampers 511a, 511b et seq. hold base plate 517 in place horizontally. When an insect lands on landing sites 510, 510a et seq. the landing is recorded electrically through a sensor shown in magnified form in FIG. 1A. The sensor which is, in fact, a transducer 513 causes an electrical impulse caused by the pressure of the insects landing to proceed through wire 518 and then through wire 519 (held in position by holder 512) to a multi-channel A-D converter 523 (using electric power supply 539). Converter 523 is associated with program tape storage 524, printer 520 and data link to digital computer 521. Thus, a recording of the data is effected. Reference numeral 522 represents a "Faraday Cage" completing the olfactometer circuit.

FIG. 1A is a partial cross section view taken along lines 1A—1A of FIG. 1 showing one specific landing site 510 having a surface on which the insect lands if attracted by such a material as 9-decen-1-ol or does not land if repelled by such a material as 9-decen-1-ol which is also located at certain other specific landing sites. At other landing sites nothing is located (and these are the "control" landing sites). The olfactometer may include base plate 526 (shown in FIG. 1B) covered by face plate 517. The base plate 526 in turn is located on dampers 511a, 511b, et seq. Face plate 517 remains covered with such a material as SARAN WRAP ® 525 (shown in FIG. 1B) which fits snugly under the landing pad 510 et seq. so that any insects that are attracted to the landing sites 510 are not distracted to any other areas on base plate 517.

FIG. 1B is an enlarged exploded view of that portion of the olfactometer apparatus which involves the provision of light and air to the insect landing sites 510, 510a, 510b et seq. particularly showing how face plate 517 is mounted on base plate 526.

FIG. 1C shows the apparatus of FIG. 1A connected and ready for use in its testing mode where spacer plate 529 is connected in a tightly fitting manner to ring 528 which, in turn, is connected in a tightly fitting manner to face plate 517 and face plate 517 is connected in a tightly fitting manner to base plate 526.

Figure 1D:
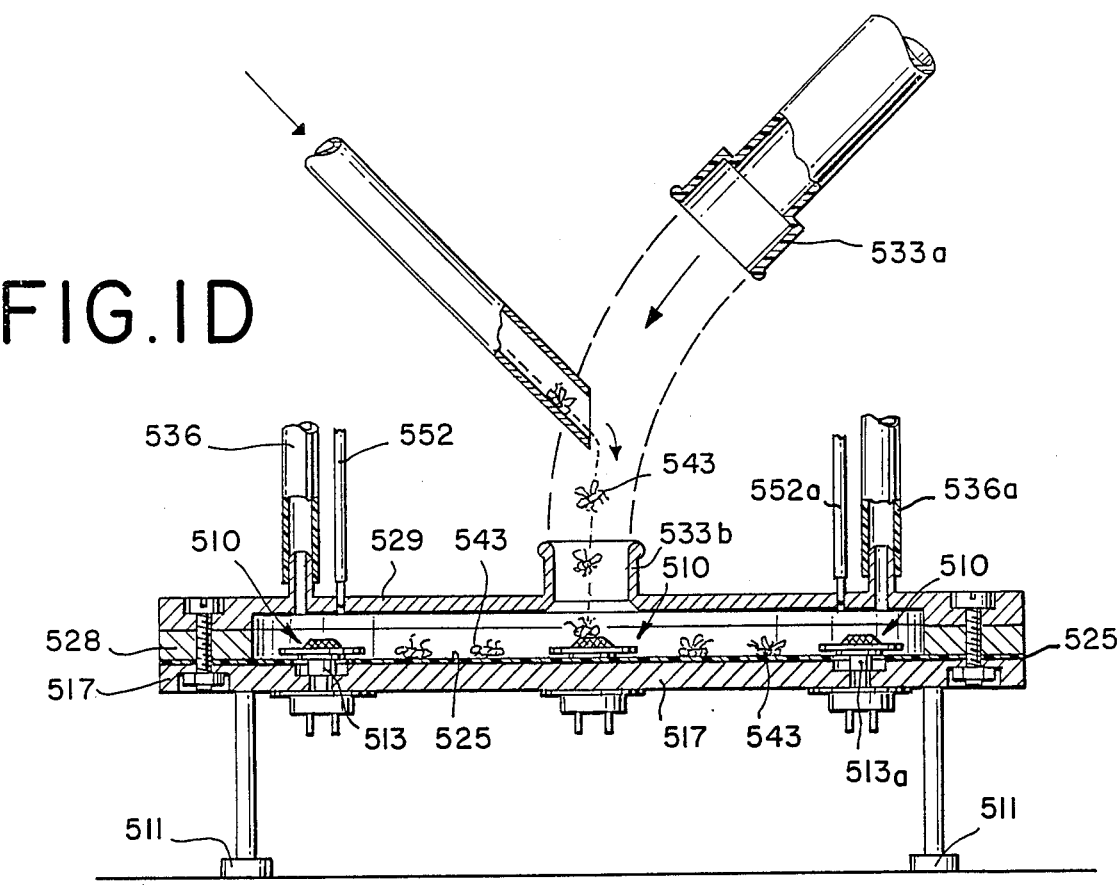
FIG. 1D is a cut-away side elevation view of the base section of the olfactometer apparatus of FIG. 1 with the air hose 533 disconnected in order to load the apparatus with cold or $CO_2$-anaesthetized insects prior to using the apparatus of FIG. 1 in order to test the attractancy or repellency of certain molecules for the said insects.
Figure 1E:
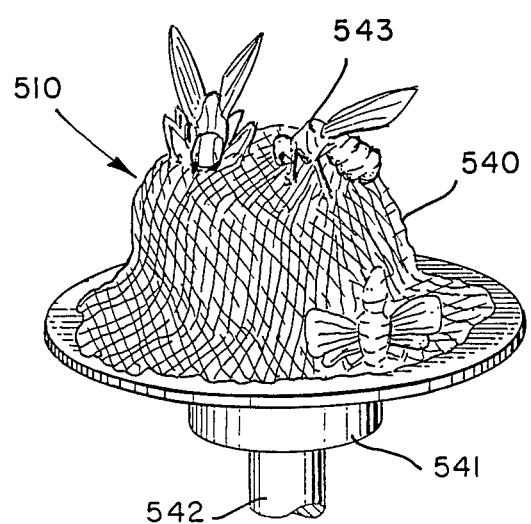
FIG. 1E is a perspective diagram of an embodiment of an insect landing pad section useful in operating the apparatus of FIG. 1 (landing pad 510) with insects 543 feeding thereon.

FIG. 1D is a cut-away side elevation view of the olfactometer apparatus of FIG. 1 being prepared for use with air hose 533a removed from air connector base 533b so that anaesthetized insects 543, e.g., anaesthetized *Musca domestica* may be placed on plate 517 prior to the testing procedure which involves the connection of air hose 533a to joint 533b. It should be noted that after the air hose 533a is connected and air is fed in through lines 536 and light is transported through light guides 552 the insects 543, 543a et seq. are de-anaesthetized and may or may not be attracted to landing sites 510, 510a et seq. as shown in detail in FIG. 1E. The landing pads are composed of a screen device ("hat") 540 underneath which is an insect nutrient source 545 (shown in FIG. 1G). The landing pad in FIG. 1D is supported by support 541 connected through shaft 542 to wire 518 which, in turn, is connected to the computer-assisted data collection and recordal mechanism.

FIG. 1F shows the olfactometer section concerning the operational part of the olfactometer in place and in operation with insects 543 attracted to pad 540 on pad 540.

FIG. 1G is a cut-away perspective view of landing pad 540 wherein the screen device which supports any attracted insects is located on support 510; and insect nutriant source 545 is shown under the sreen.

FIGS. 2A, 2B, 2C and 2D are exploded views of a second embodiment of the olfactometer apparatus of our invention used in testing, the efficacy of the $C_8$-t-alkanols and $C_5$-$C_{11}$-omega-alken-1-ols of our invention as house fly (*Musca domestica*) attracting materials. Air source 634 feeds air through line 635 through air distributors 636, 636a et seq. onto base plate 617 containing insect landing sites 610, 610a et seq. The landing sites 610 and 610a are shown in detail in FIGS. 2F, 2G, 2J and 2K. The base plate 617 is separated from the spacer plate 629 for the air lines 636 whereby the air lines 636 are held in place at positions 631, 631a et seq. Air exists through line 633a using exhaust fan 633.

Simultaneously with the air being fed through lines 636, 636a et seq. from air source 634, light is guided through light guides 652 and 652a exemplified, infra, using light source 651 powered by electrrc power source 650. The base plate 617 is separated from the spacer plate 629 also for the light guides 652, 652a et seq. whereby the light guides 652, 652a et seq. are held in place at positions 631, 631a et seq.

The olfactometer is assisted with computer apparatus shown in schematic form and block flow diagram form using reference numerals 620, 621, 623, 624 and 639. Dampers 611a, 611b et seq. hold base plate 617 in place horizontally.

When an insect 643 de-anaestetized and in action in 3-space 646 (in an area defined according to x, y and z coordinates), e.g., a house fly (*Musca domestica*)(shown in FIG. 2E) lands on a sensor landing site, the landing is recorded electrically through the sensor 610, 610a et seq. shown in magnified form in FIGS. 2F, 2G, 2J and 2K. The sensor 610, 610a et seq. causes an electrical impulse to proceed through wire 618 and then through wire 619 (using electric power source 639) to a multi-channel A-D converter 623 which is associated with program tape storage 624, printer 620 and digital computer associated with modem and main frame 621. Reference numeral 622 indicates the completion of the circuit for the olfactometer as a "Faraday Cage". Spacer ring 628 separates spacer plate 629 from the face plate 617. The spacer ring 628 (when the olfactometer is ready to use) is held sealably in place on the sensor devices 610 as a result of the inclusion of silicone seals 649 which are located on each of the sensors and are also located on base plate 617. The silicone seals are shown in detail by reference numeral 649 on FIG. 2F. In the embodiment of the olfactometer of our invention shown in FIGS. 2A, 2B, 2C and 2D, spacer 628 is fitted onto the silicone seals 649 which are located not only on sensors 610 but also on face plate 617. Preferably, face plate 617 is mounted on base plate 626 which may, if desired, contain a cavity 657 for a fluid heating coil (as illustrated in FIGS. 3, 4 and 4A).

Figure 2A:
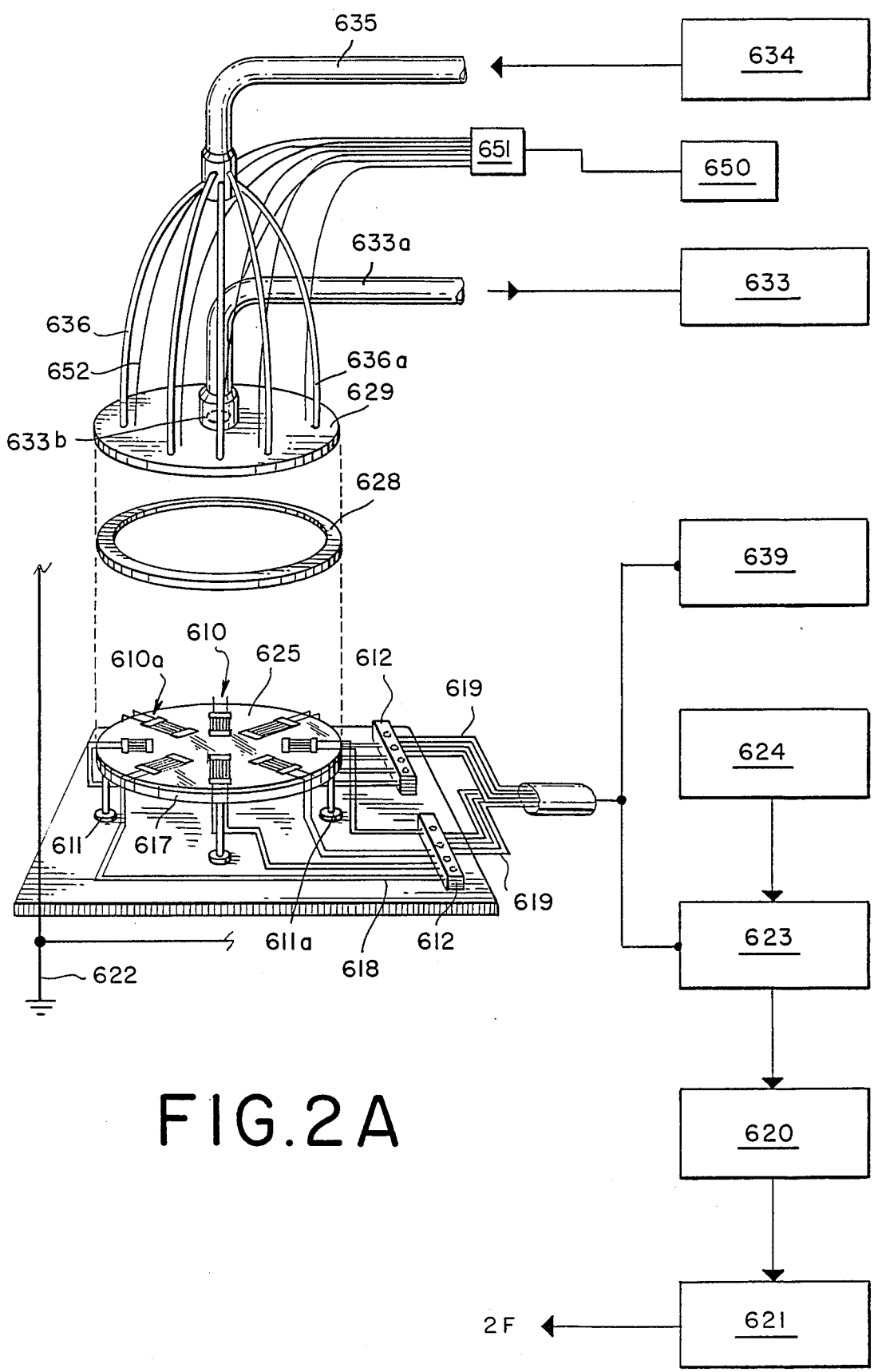
FIG. 2A is a schematic diagram (exploded for illustration purposes) of a second embodiment of the olfactometer apparatus $C_8$-t-alkanols and $C_5$-$C_{11}$-omega-alken-1-ols of our invention as attractants for house flies (*Musca domestica*) indicating in schematic block flow diagram form the utilization of computer-assisted efficacy measuring appartus.
Figure 2C:
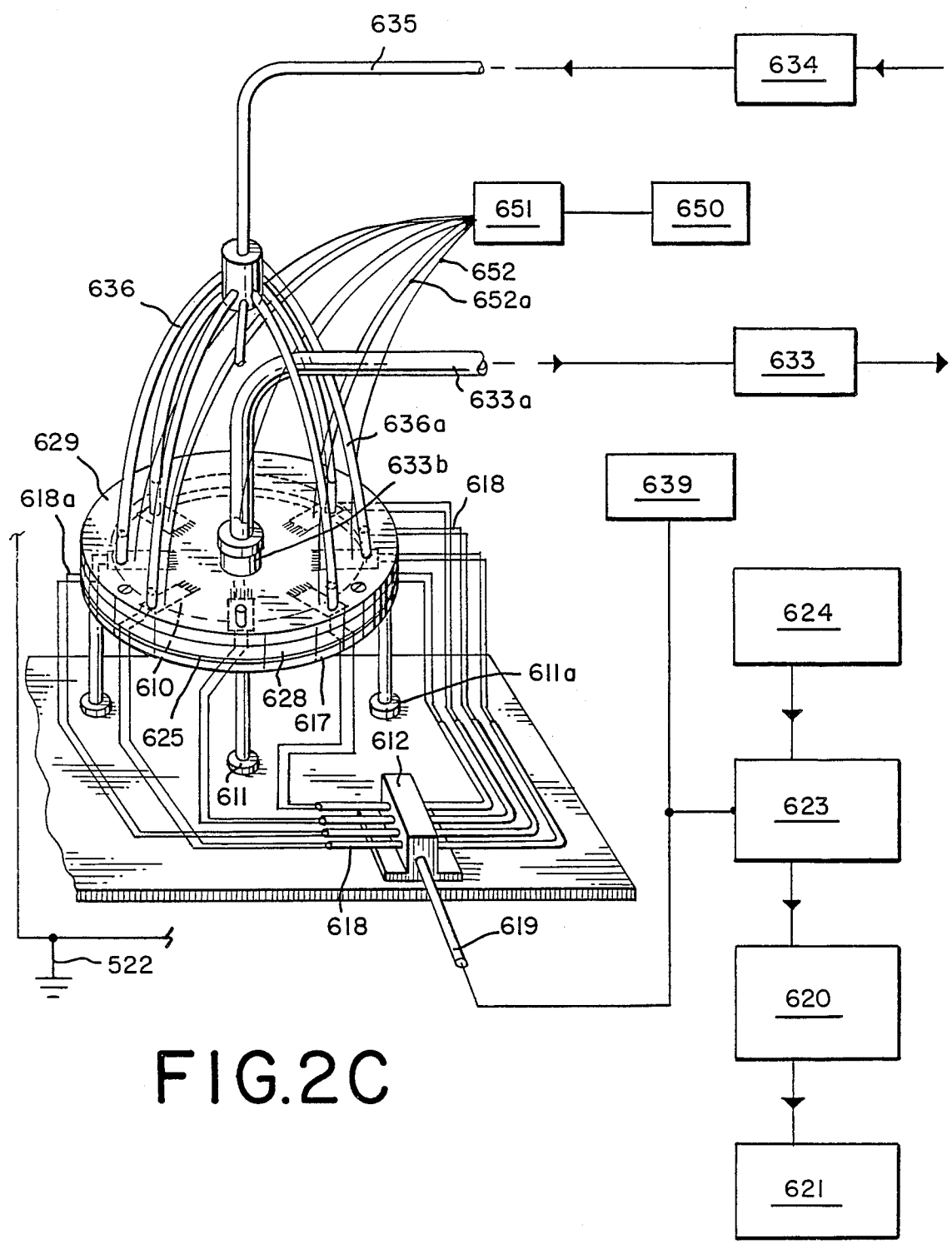
FIG. 2C is a schematic diagram of the embodiment of the olfactometer apparatus of FIG. 2A (shown ready for operation) useful, inter alia, in ascertaining the efficacy of the $C_8$-t-alkanols and $C_5$-$C_{11}$-omega-alken-1-ols of our invention as attractants for house flies (*Musca domestica*) indicating in schematic block flow diagram form the utilization of computer-assisted efficacy measuring apparatus.
Figure 2D:
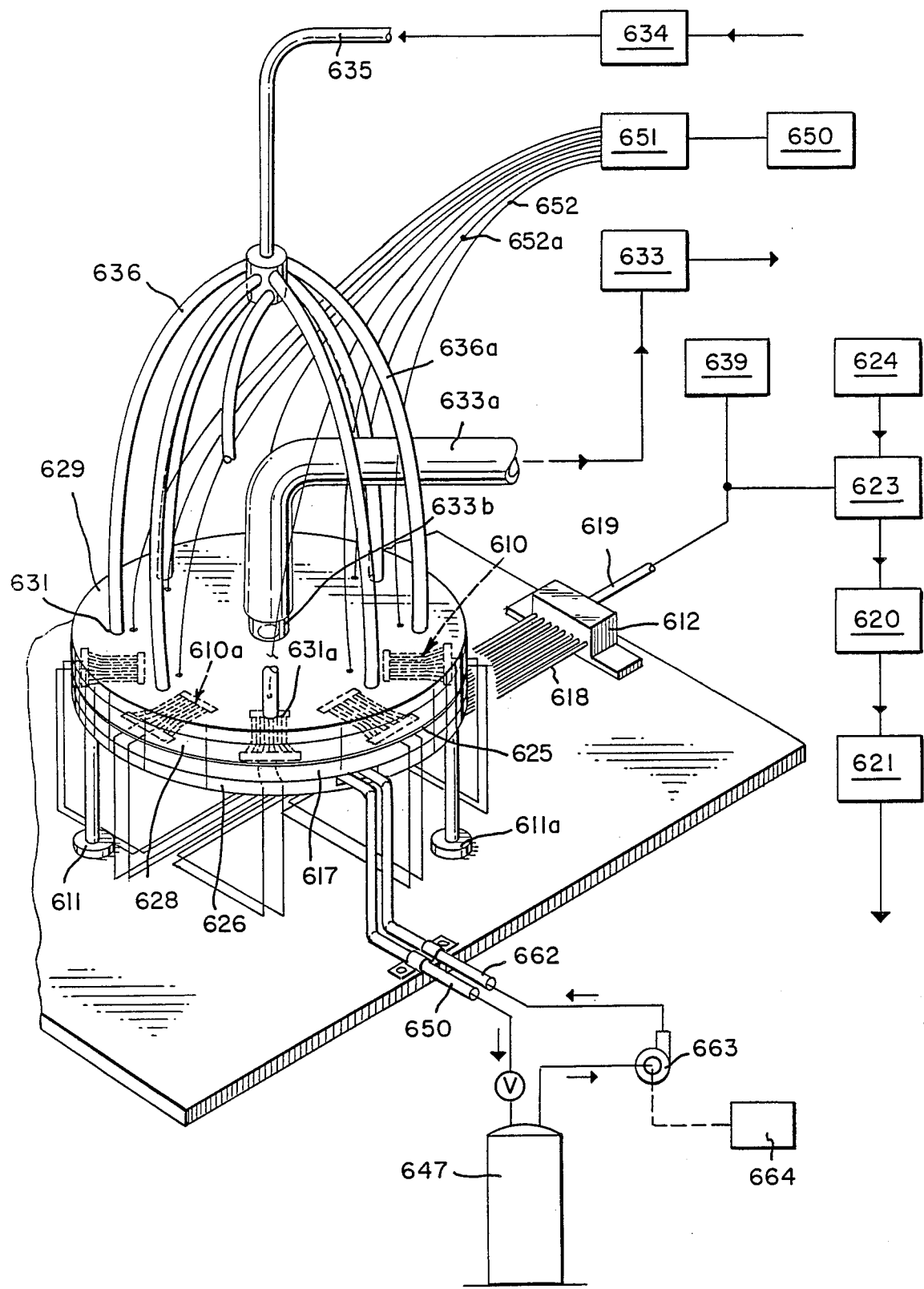
FIG. 2D is a schematic diagram of a third embodiment of the olfactometer apparatus of our invention (ready for operation) useful in ascertaining the efficacy of the $C_8$-t-alkanols and $C_5$-$C_{11}$-omega-alken-1-ols of our invention as attractants for house flies (*Musca domestica*), and also indicating in schematic block flow diagram form the utilization of computer-assisted efficacy measuring apparatus.
Figure 2E:
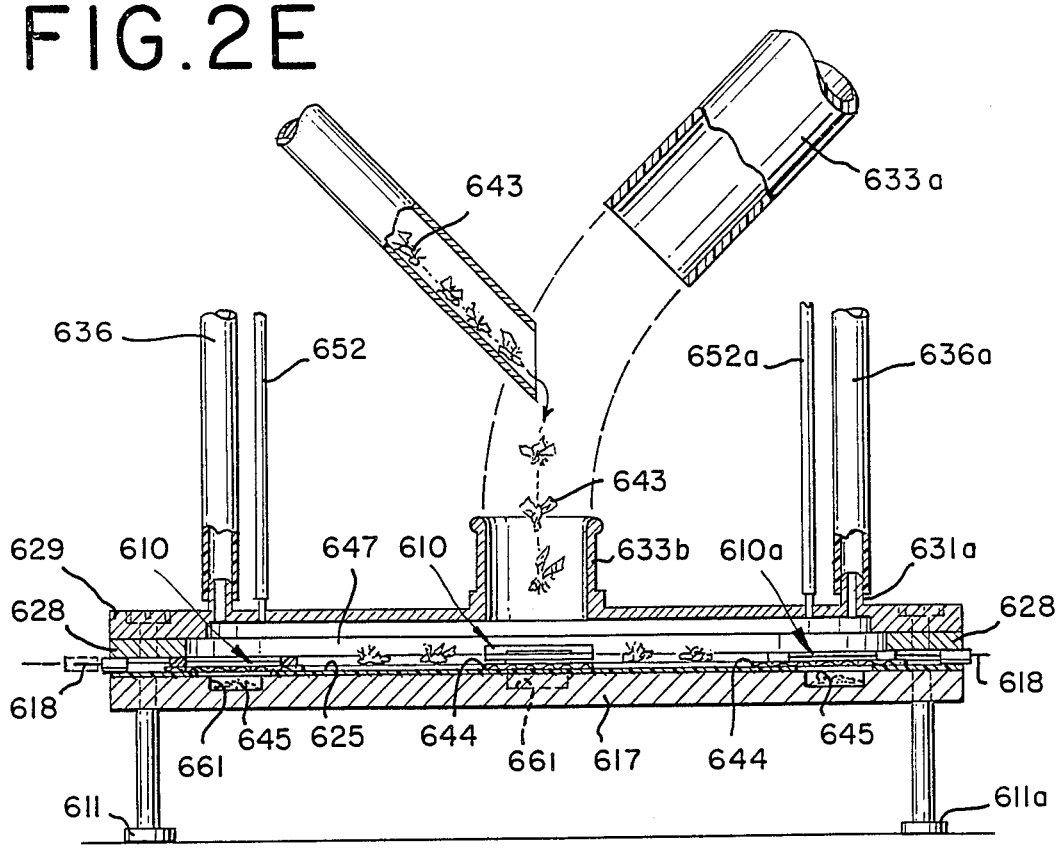
FIG. 2E is a cut-away side elevation view of the base section of the operational part of the olfactometer apparatus of FIG. 2A with air hose 633a disconnected for the purpose of placing cold or $CO_2$-anaesthetized insects onto the base of the apparatus prior to operating the apparatus for the purpose of determining insect attractancy or repellency.
Figure 2F:
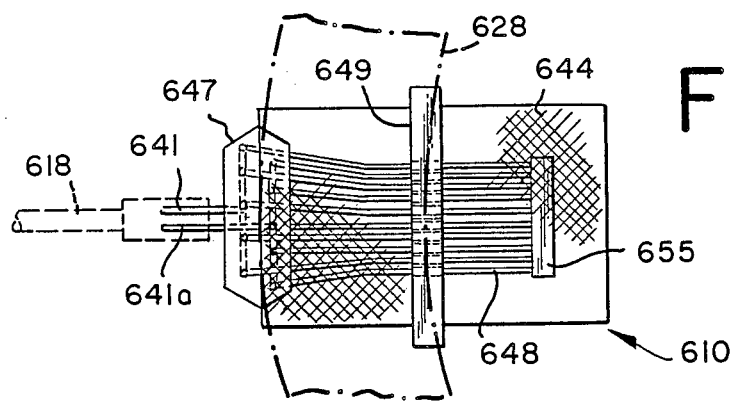
FIG. 2F is a top view of an insect feeding surface comprising spaced electrically conductive wires mounted on a silicone membrane and used in the embodiment of the olfactometer apparatus as illustrated in FIGS. 2A, 2B, 2C, 2D and 2E.
Figure 2G:
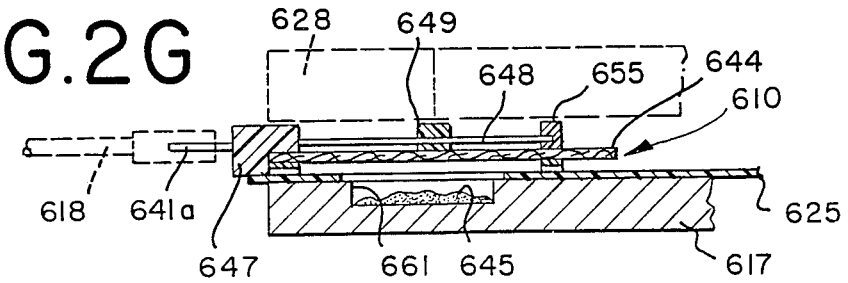
FIG. 2G is a cut-away side elevation view of the insect feeding surface comprising spaced electrically conductive wires of FIG. 2F.
Figure 2H:
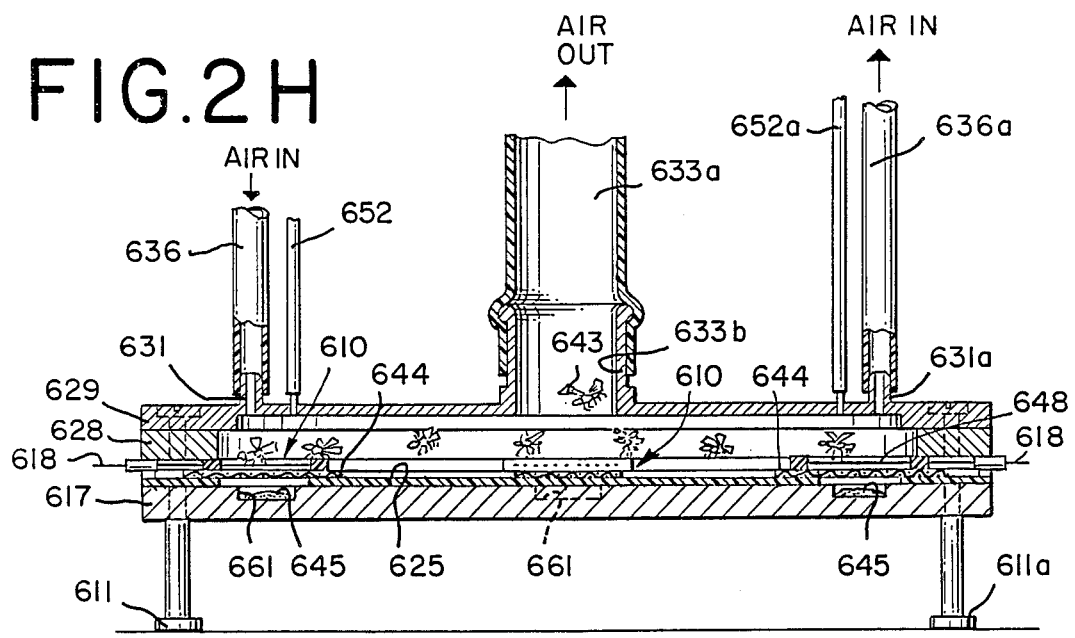
FIG. 2H is a cut-away side elevation view of the base section of the apparatus of FIG. 2D showing air hose 633a connected and the apparatus in operation with insects 643 located on the insect feeding surface comprising spaced electrically conductive wires.
Figure 2J:
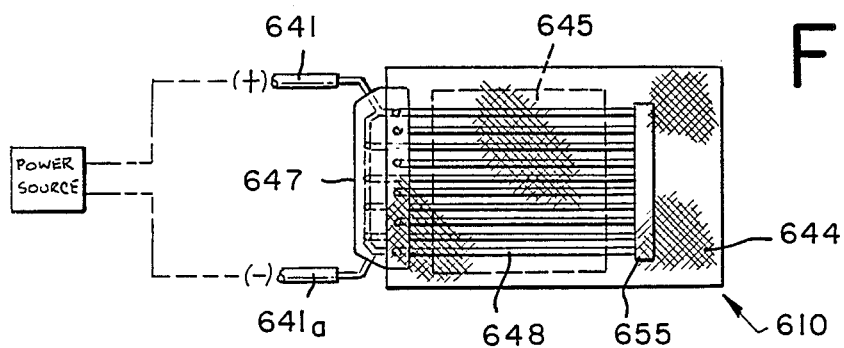
FIG. 2J is a top view of a second embodiment of the insect feeding means 610 comprising spaced electrically conductive wires.
Figure 2K:
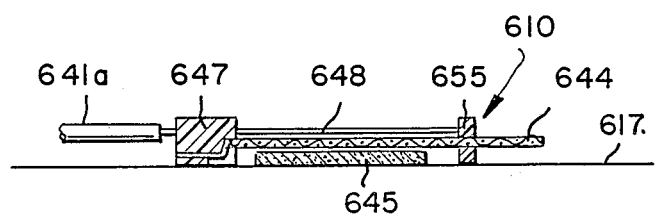
FIG. 2K is a cut-away side elevation view of the insect feeding means of FIG. 2J.

Referring to FIGS. 2E, 2F and 2G, the insect feeding surface in this second embodiment of our invention comprises a number of spaced electrically conductive wires 648 held in place by holders 647 and 655 and coated with a silicone resin for sealing purposes 649. Wires 648 are combined into positive leads 641 and negative leads 641a. The wires 648 are held in place above a membrane 644, actually a silicone membrane as described in detail in the Davis, et al paper (J. Med. Entomol. Volume 20, No. 2: 177-182) and the Butler, et al paper in ACAROLOGY VI, Volume 2 cited, supra (indicated as a "Reinforced Silicone Membrane"). Beneath this membrane 644 is the insect nutrient composition of matter or insect food 645 as shown specifically in FIG. 2G. Also holding the wires in place is holder 647 shown in detail in FIG. 2G.

Prior to operation of the olfactometer for testing the insects for attractancy to certain molecules, e.g., 3-ethyl-2-methyl-3-pentanol, air hose 633a is disconnected from joint 633b in order to place anaesthetized (via $CO_2$) insects 643 onto surface 617. After the insects 643 are placed on surface 617 air hose (for the purposes of air exhaust) 633a is connected at joint 633b in an air tight manner and air is passed through lines 636, 636a et seq. and simultaneously light is radiated through light guides 652, 652a et seq., thus de-anaesthetizing the insects and causing them to be either attracted or not to the proximity or surface of wires 648. Even if the insects are attracted to the proximity of wires 648 an electric field is generated thereby giving rise to an electric current in wires 618 (due to the close spacing of the wires 648) thereby causing a "readout" from the computer system.

Figure 3:
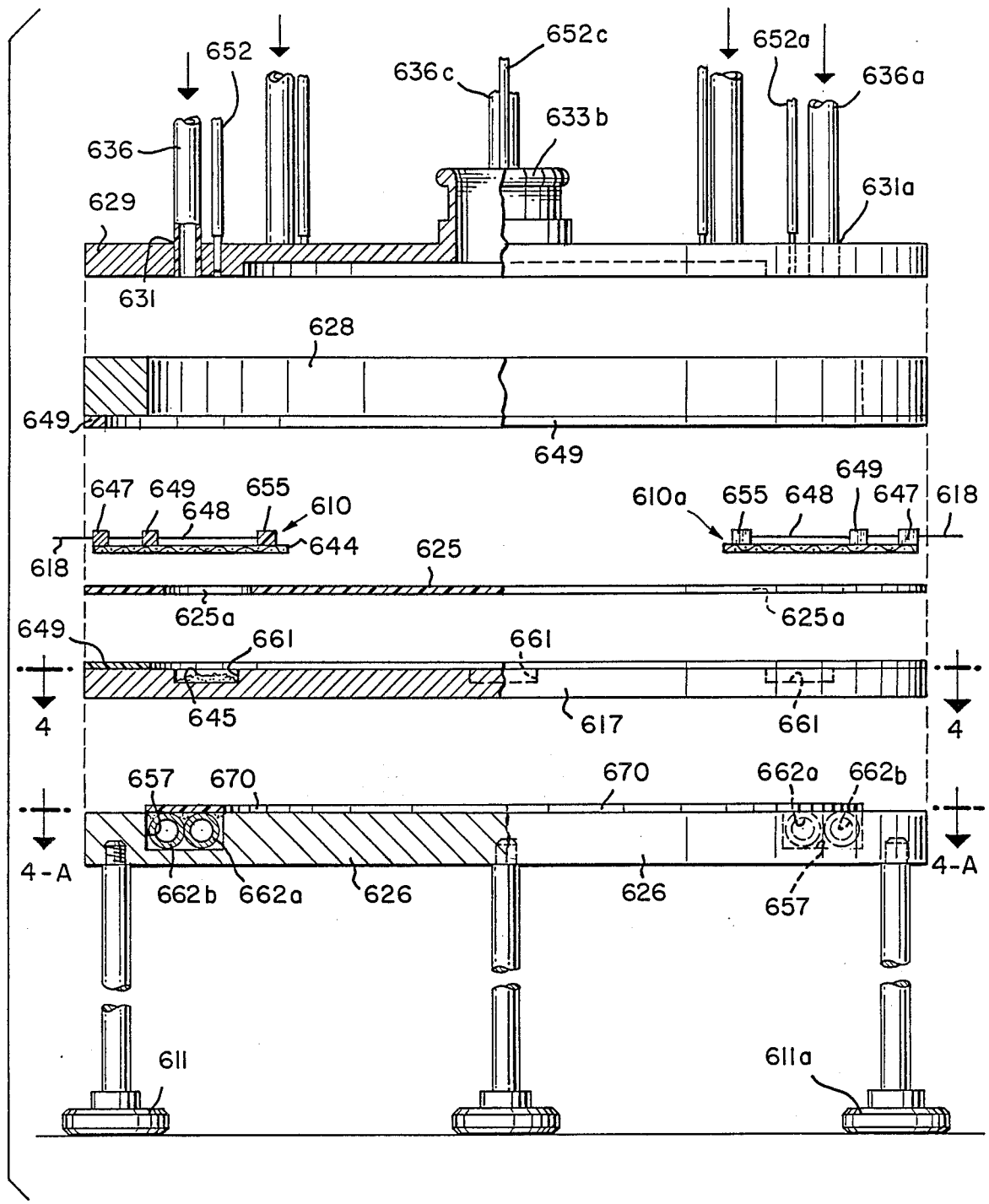
FIG. 3 is a schematic diagram (blown up for illustration purposes) of a cut-away side elevation view of a section of the olfactometer apparatus of the embodiment of FIG. 2D useful in ascertaining, the efficacy of the $C_8$-t-alkanols and $C_5$-$C_{11}$-omega-alken-1-ols of our invention as attractants for house flies (*Musca domestica*) without indicating the utilization of the computer-assisted efficacy measuring apparatus; but only indicating a section of the operational portion of the olfactometer apparatus.
Figures 4, 4A:
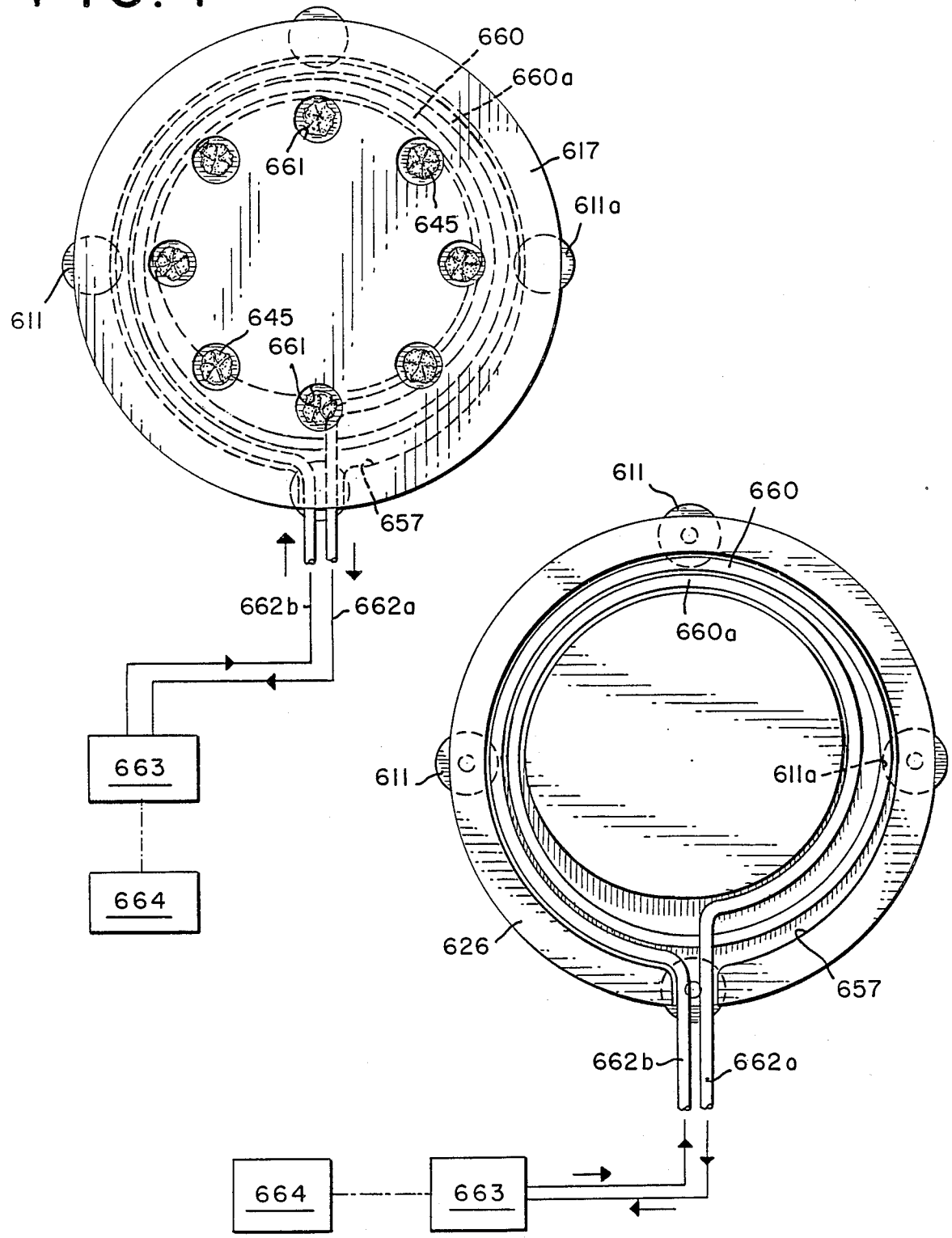
FIG. 4 is the top view of the lower section of an embodiment of the olfactometer apparatus of FIG. 2D, looking down at facing plate 617, indicating in schematic block flow diagram form the utilization of heat transfer and forced fluid flow apparatus in schematic block flow diagram form.
FIG. 4A is another top view of the lower section of the olfactometer apparatus of FIG. 2D looking down at base plate 625 and at heating coils 660 and 660a indicating in schematic block flow diagram form heat transfer and forced fluid flow apparatus.

FIG. 3 is a cut-away side elevation schematic view of a detailed section of the olfactometer of our invention and is in fact a third embodiment of the olfactometer used in the development of our invention indicating the presence of heating coils 650 and 662 in base plate 626. Air is fed in through lines 636 while light is radiated through light guide 652 both held in place on plate 629. Plate 629 is spaced at a reasonable distance (e.g., 1.0") using spacer ring 628 which is sealed in place via silicone seals 649. The silicone seals 649 are, for example, holding sensor 610 in place. Sensor 610 is located on silicone membrane 644 and is located on a thin polymeric continuous film, e.g., SARAN WRAP ® 625 which is located on face plate 617. The SARAN WRAP ® contains a plurality of radially spaced openings 625 directly corresponding to feed wells 661. Thus, face plate 617 contains a well for liquid feeds 661 which is situated directly beneath the location of sensors 610. Face plate 617 is preferably constructed of aluminum. Face plate 617 is in direct face-to-face contact with base plate 626 which contains cavity 657 for heating coils 650 and 662. Base plate 626 is located on a stand which is situated on dampers 611. The top view of the olfactometer looking directly down on face plate 617 is set forth in FIG. 4. The reference numeral 617 refers to the face plate per se. Wells for liquid feeds 661 are shown on face plate 617. Hidden lines 660 and 660a are representations of the heating coils through which heat transfer fluid is supplied through lines 650 and 662 (with heated water) using pump 663 the heat for which is controlled using controller 664. Coils 650 and 662a are preferably covered at cavity 657 with a heat transfer paste 670.

FIG. 4A is also a top view of the olfactometer with the face plate removed looking directly down on the base plate 626.

FIG. 5 is a exploded view of a fourth embodiment of the olfactometer apparatus used in testing the efficacy of, inter alia, 10-undecen-1-ol as a house fly (*Musca domestica*) attracting material. Air source 734 feeds air through line 735 through air distributors 736, 736a et seq. onto base plate 717 containing insect landing sites 710, 710a et seq. The base plate 717 is separated from the spacer plate 729 for the air lines 736, 736a et seq. whereby the air lines 736, 736a et seq. are held in place at positions 731 and 731a. Air exits through line 733a using exhaust fan 733. The olfactometer is assisted with computer apparatus shown in schematic form and block flow diagram form using reference numeral 720, 721, 723, 724 and 739. Dampers 711a, 711b et seq. hold base plate 717 in place horizontally. When an insect lands on sensor landing site 710, 710a et seq. the landing is recorded electrically through a sensor shown in magnified form in FIG. 5A. The sensor landing site includes a transducer 713 and causes an electrical impulse to proceed through wire 718 and then through wire 719 to a multi-channel A-D converter 723 (using electric power source 739) which is associated with program tape storage 724, printer 720 and digital computer which is associated with modem and main frame 721. Reference numeral 722 shows a "Faraday" cage completing the olfactometer circuit. The electric impulse thus effects a recording of the data as set forth in Table I, supra.

FIG. 5A is a partial cross section taken along lines 5A—5A of FIG. 5 showing one specific landing site 710a on which the insect lands if attracted by one of the $C_8$-t-alkanols and $C_5$-$C_{11}$-omega-alken-1-ols of our invention or does not land if repelled by one or more of the $C_8$-t-alkanols and $C_5$-$C_{11}$-omega-alken-1-ols of our invention which is also located at specific landing sites. At other landing sites nothing is located (and these are the "control" landing sites). The olfactometer includes a base 781 on which the damper 711a, 711b et seq. are located, namely base 781. Base plate 717 is preferably covered with a film such as SARAN WRAP ® 725 so that any insects that are attracted to the landing sites are not distracted to any other areas on base plate 717.

Figure 6:
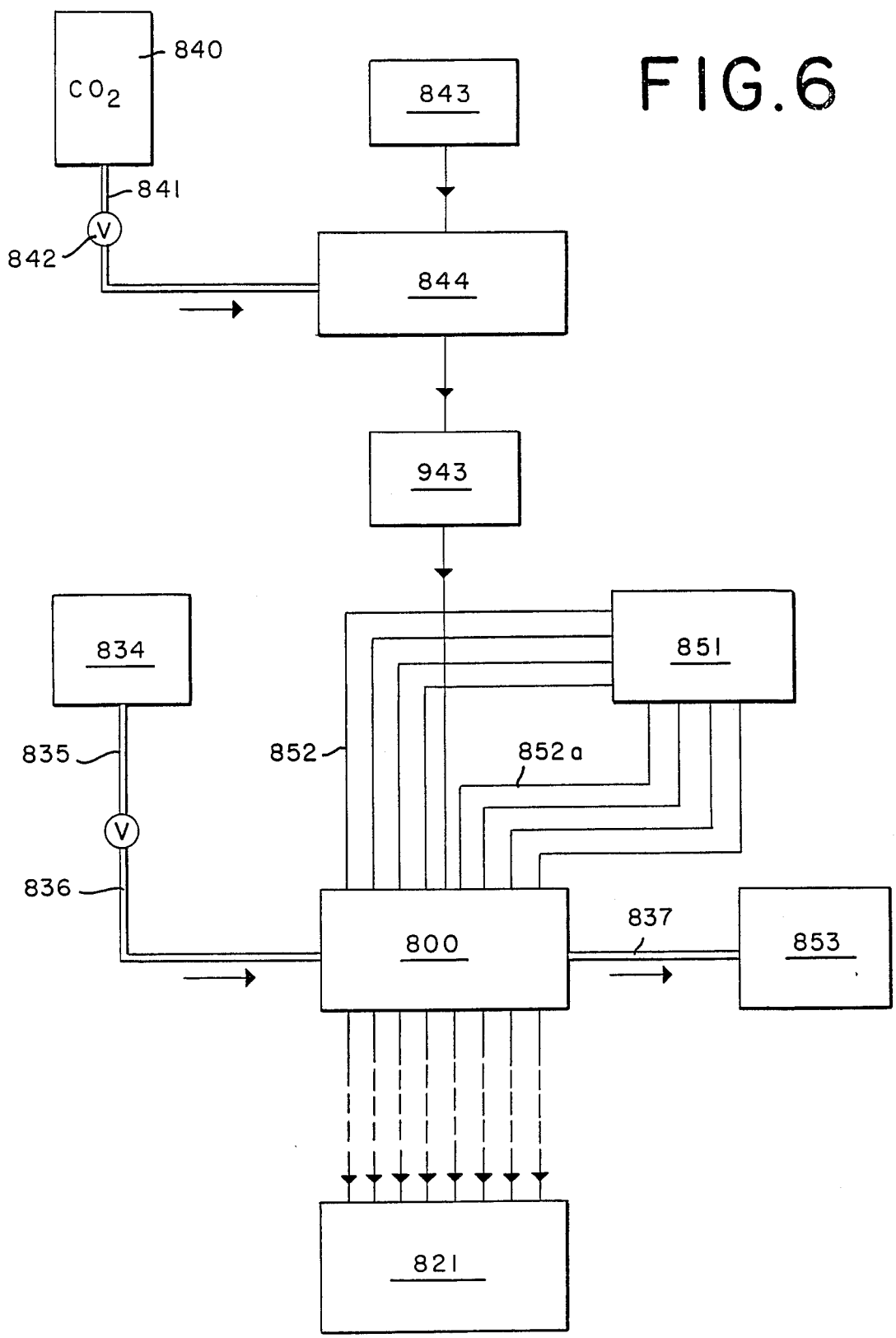
FIG. 6 is a schematic block flow diagram setting forth the process of our invention for testing repellency and attractancy of molecules using such apparatus as is set forth in FIGS. 1, 2A, 2D and 5.

FIG. 6 is a block flow schematic diagram indicating the process used in reducing our invention to practice. Insects 843 are anaesthetized at 844 using anaesthetizing cooling or anaesthetizing gas 840 passed through lines 841 and valve 842. The anaesthetized insects at 943 are placed in testing apparatus 800. The testing apparatus is closed except for introduction of air and, optionally light. Air at 834 is passed through line 835 past valve 836 into the testing apparatus with, optionally light from source 851. The air leaves the testing apparatus through line 837 into evacuation chamber 833. When the air is passed through the testing apparatus with, optionally, light, the insects are de-anaesthetized and are attracted to attraction sites, if, indeed, the molecules at the attraction sites attract the insects. When the insects are near or on the attraction sites, the attraction sites cause an impulse into a computer system which records data at 821.

FIG. 7 is a schematic cut-away elevation diagram of the extrusion and pelletizing apparatus useful in carrying out a process used in reducing our invention to practice. During the operation of said apparatus, motor 15 drives the extruder screws located at 23A in barrel 16, the extruder being operated at temperatures in the range of about 150° up to about 250° C. At the beginning of the barrel, resin at source 12 together with processing aids at location 13 is added via addition funnel 14 into the extruder. Simultaneously (when the operation reaches "steady state"), one or more of the $C_8$-t-alkanols and $C_5$-$C_{11}$-omega-alken-1-ols of our invention is added to the extruder at two or more of barrels S-3, S-4, S-5, S-6, S-7 and S-8 of the extruder (which may be a twin screw or single screw extruder) at locations 18a, 18b, 18c and 18d, for example, by means of gear pump 23 from source 17. From source 19 into barrel segments S-5, S-6, S-7, S-8, S-9 and S-10, optionally, the gaseous or liquid blowing agents, e.g., nitrogen, carbon dioxide and the like as described, supra, are added simultaneously with the addition of one or more of the $C_8$-t-alkanols and $C_5$-$C_{11}$-omega-alken-1-ols of our invention. The feed rate range of resin is about 80–300 pounds per hour. The feed rate range of one or more of the $C_8$-t-alkanols and $C_5$-$C_{11}$-omega-alken-1-ols of our invention is between 1 and 35% of the feed rate range of the resin. The blowing agent rate range (when the blowing agent is used) is such that the pressure of the gas or the pressure over the liquid being fed into the extruder is between about 50 and 200 psig. If desired, the extruded ribbon or cylinder may be passed through water bath 20 and pelletizer 21 into collection apparatus 21a.

TABLE I

| Composition | Description of Composition |
| --- | --- |
| "A" | No compounds in airstream. |
| "B" | Tagetone, 0.001% (in triethyl citrate). |
| "C" | 3-Ethyl-3-hexanol. |

TABLE I-continued

| Composition | Description of Composition |
| --- | --- |
| "D" | 3-Ethyl-2-methyl-3-pentanol. |
| "E" | 1-Nonen-3-ol. |
| "F" | Standard attractant; extract of used fly rearing media (mixture of anures, alfalfa, fish meal and baking soda). |
| "G" | 9-Decen-1-ol. |
| "H" | 10-Undecen-1-ol. |

Also tested was n-dodecanol for its properties as an insect attractant or insect repellent in apparatus set forth in FIGS. 1, 2, 3 and 4 of application for U.S. patent, Ser. No. 930,418 filed on Nov. 14, 1986, the specificaton of which is incorporated herein by reference.

The summary of the attractancy and repellency for the *Musca domestica* (Diptera:Muscidae) for Substances "A", "B", "C", "D", "E", "F", "G" and "H" and for n-dodecanol is summarized as follows:

TABLE II

| Substance | Description of Attractancy Or Repellency For *Musca Domestica* L. (*Diptera:Muscidae*) |
| --- | --- |
| "A" | Control |
| "B" | Attractant |
| "C" | Attractant |
| "D" | Attractant |
| "E" | Repellent activity; the best repellent in the trials. |
| "F" | Standard attractant. |
| "G" | Attractancy at a higher rate than attractant "D"; but less attractive than attractant "F"; but much more attractive than Substance "E". |
| "H" | Strong repellency for 30 minutes of exposure; then shifting to strong attractancy; as attractive or more attractive than Substance "F" after 30 minutes (as confirmed by Table IV, V and VI on page 49, et seq). |
| N—dodecanol | Attractancy equal to or better than Substance "F". |

During the first 10 minutes of testing, Substance "E" and Substance "H" have repellency which could be considered to be equivalent to one another. After that, Substance "H" is 10–20 times more attractive for *Musca domestica L.* than substance "E".

FIG. 8A is a series of graphs, depicted in three dimensions (in a circular mode (t[time]=0 at center of circle) for the "x" and "y" axes) showing the relative attractiveness or repellency of the $C_8$-t-alkanols and $C_5$-$C_{11}$-omega-alken-1-ols of our invention compared with a repellent, 1-nonen-3-ol, a known attractant, tagetone having the structure:

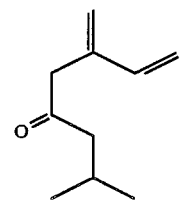

(0.001% in triethyl citrate) and another known attractant, "extract of used fly rearing media" (mixture of manures, alfalfa and baking soda). The graphs are based on experiments run for a total of 20 hours with six intervals of 3.67 hours each. The results are tabulated in the following Table III:

TABLE III

| Channel | Sample Code | Insects Collected Per Interval | | | | | |
|---|---|---|---|---|---|---|---|
| channel 41 | sample D | 0 | 300 | 60 | 35 | 37 | 17 | 26 |
| channel 42 | sample G | 0 | 296 | 101 | 150 | 162 | 143 | 130 |
| channel 43 | sample E | 0 | 146 | 40 | 45 | 31 | 28 | 28 |
| channel 44 | sample F | 0 | 593 | 198 | 287 | 383 | 496 | 556 |
| channel 45 | sample C | 0 | 421 | 85 | 106 | 83 | 77 | 91 |
| channel 46 | sample A | 0 | 191 | 39 | 43 | 54 | 65 | 79 |
| channel 47 | sample B | 0 | 414 | 90 | 93 | 63 | 59 | 68 |
| channel 48 | sample H | 0 | 211 | 37 | 25 | 23 | 23 | 27 |

The presentation of data in FIG. 8A as well as FIGS. 8B–11D (inclusive) substantially follows the technique published by Mittler, et al "ANNUAL REVIEW OF ENTOMOLOGY", Volume 32, 1987, pages 17–48 [article entitled "CHEMOSYSTEMATICS AND EVOLUTION OF BEETLE CHEMICAL DEFENSE"] the disclosure of which is incorporated by reference herein.

The graph indicated by reference numeral 41 is the graph for 3-ethyl-2-methyl-3-pentanol. The graph indicated by reference numeral 42 is the graph for 9-decen-1-ol. The graph indicated by reference numeral 43 is the graph for 1-nonen-3-ol, a repellent. The graph indicated by reference numeral 44 is the graph for the standard attractant, extract of used fly rearing media. The graph indicated by reference numeral 45 is the graph for 3-ethyl-3-hexanol. The graph indicated by reference numeral 46 is a graph showing the results with no treatment compound in the airstream. The graph indicated by reference numeral 47 is the graph for tagetone, 0.001% in triethyl citrate; tagetone being a known attractant for *Musca domestica* L. (Diptera:Muscidae). The graph indicated by reference numeral 48 is the graph for 10-undecen-1-ol.

FIG. 8B is a series of graphs, depicted in three dimensions (in a rectangular mode for the "x" and "y" axes) showing the relative attractiveness or repellency of the $C_8$-t-alkanols and $C_5$–$C_{11}$-omega-alken-1-ols of our invention compared with a repellent, 1-nonen-3-ol, a known attractant, tagetone (0.001% in triethyl citrate), and another known attractant, "extract of used fly rearing media" (mixtures of manures, alfalfa and baking soda). The graphs are based on experiments run for a total of 20 hours with six intervals of 3.67 hours each. The results are tabulated in Table III set forth, supra.

The graph indicated by reference numeral 51 is the graph for 3-ethyl-2-methyl-3-pentanol, an attractant. The graph indicated by reference numeral 52 is the graph for 9-decen-1-ol, an attractant. The graph indicated by reference numeral 53 is the graph for 1-nonen-3-ol, a repellent. The graph indicated by reference numeral 54 is the graph for the standard attractant, the "extract of used fly rearing media". The graph indicated by reference numeral 55 is the graph for 3-ethyl-3-hexanol, an attractant. The graph indicated by reference numeral 56 is the graph for treatment with no compound in the airstream. The graph indicated by reference numeral 57 is the graph for tagetone (0.001% in triethyl citrate), an attractant. The graph indicated by reference numeral 58 is the graph for 10-undecen-1-ol. The graph indicated by reference numeral 61 is the graph for 3-ethyl-2-methyl-3-pentanol, an attractant. The graph indicated by reference numeral 68 is the graph for 10-undecen-1-ol (a duplicate).

FIG. 8C is a depiction of a replicate of the data presented in FIG. 8A and is a series of graphs depicted in three dimensions (in a circular mode for the "x" and "y" axes) showing the relative attractancies or repellencies of the $C_8$-t-alkanols and $C_5$–$C_{11}$-omega-alken-1-ols of our invention compared with a repellent 1-nonen-3-ol, a known attractant tagetone (0.001% in triethyl citrate and another known attractant, extract of used fly rearing media"(mixtures of manures, alfalfa and baking soda). The graph indicated by reference numeral 71 is the graph for 3-ethyl-2-methyl-3-pentanol, an attractant. The graph indicated by reference numeral 72 is the graph for 9-decen-1-ol. The graph indicated by reference numeral 73 is the graph for 1-nonen-3-ol, a repellent. The graph indicated by reference numeral 74 is the graph for the standard attractant, the "extract of used fly rearing media". The graph indicated by reference numeral 75 is is the graph for 3-ethyl-3-hexanol, an attractant. The graph indicated by reference numeral 76 is the graph for a treatment with no compound in the airstream. The graph indicated by reference numeral 77 is the graph for tagetone (concentration: 0.001% in triethyl citrate). The graph indicated by reference numeral 78 is the graph for 10-undecen-1-ol.

FIG. 8D is the series of graphs of FIGS. 8A and 8C with the data thereof depicted in two dimensions. Thus, the graphs indicated by reference numerals 81A and 81B are the graphs for 3-ethyl-2-methyl-3-pentanol, an attractant. The graphs indicated by reference numerals 82A and 82B are the graphs for 9-decen-1-ol. The graphs indicated by reference numerals 83A and 83B are the graphs for 1-nonen-3-ol, a repellent. The graphs indicated by reference numerals 84A and 84B are the graphs for the standard attractant, "extract of used fly rearing media". The graphs indicated by reference numerals 85A and 85B are the graphs for 3-ethyl-3-hexanol, an attractant. The graphs indicated by reference numerals 86A and 86B is the graph showing the results from the use of no compound in the airstream. The graph indicated by reference numeral 87A and 87B are the graphs for tagetone (concentration: 0.001% in triethyl citrate), tagetone being an attractant for *Musca domestica* L. (Diptera:Muscidae).

The graphs indicated by reference numerals 88A and 88B are the graphs for the compound 10-undecen-1-ol.

FIG. 9A is a series of graphs, depicted in three dimensions (in a circular mode for the "x" and "y" axes) showing the relative attractiveness or repellency of the $C_8$-t-alkanols and $C_5$–$C_{11}$-omega-alken-1-ols of our invention compared with a repellent, 1-nonen-3-ol, a known attractant, tagetone (concentration: 0.001% in triethyl citrate) and another known attractant, "extract of used fly rearing media" (mixtures of manures, alfalfa and baking soda). The graphs are based on experiments run for a total of one hour with six (6) intervals of 10 minutes each. The results are tabulated in Table IV as follows:

TABLE IV

| Channel | Sample Code | Insects Collected Per Interval (Collection of *Musca domestica* L. (Diptera:Muscidae)) | | | | | |
|---|---|---|---|---|---|---|---|
| channel 91 | sample D | 0 | 219 | 430 | 195 | 141 | 278 | 167 |
| channel 92 | sample G | 0 | 158 | 868 | 460 | 115 | 109 | 291 |
| channel 93 | sample E | 0 | 2 | 232 | 277 | 209 | 215 | 24 |
| channel 94 | sample F | 0 | 265 | 505 | 469 | 257 | 559 | 247 |
| channel 95 | sample C | 0 | 53 | 0 | 4 | 6 | 166 | 91 |
| channel 96 | sample A | 0 | 79 | 112 | 182 | 121 | 176 | 186 |
| channel 97 | sample B | 0 | 215 | 359 | 246 | 278 | 314 | 136 |

TABLE IV-continued

| Channel | Sample Code | Insects Collected Per Interval (Collection of *Musca domestica* L. (Diptera:Muscidae)) | | | | | |
| --- | --- | --- | --- | --- | --- | --- | --- |
| channel 98 | sample H | 0 | 1 | 18 | 163 | 677 | 378 171 |

The graph indicated by reference numeral 91 is the graph for 3-ethyl-2-methyl-3-pentanol, an attractant. The graph indicated by reference numeral 92 is the graph for 9-decen-1-ol. The graph indicated by reference numeral 93 is the graph for 1-nonen-3-ol, a repellent. The graph indicated by reference numeral 94 is the graph or the standard attractant, "extract of used fly rearing media". The graph indicated by reference numeral 95 is the graph for 3-ethyl-3-hexanol, an attractant. The graph indicated by reference numeral 96 is the graph for data (*Musca domestica* L. collected per interval) when no compound is in the airstream on operation of the apparatus of FIG. 1. The graph indicated by reference numeral 97 is the graph for the compound tagetone at a concentration: 0.001% in triethyl citrate. The graph indicated by reference numeral 98 is the graph for the compound 10-undecen-1-ol demonstrating strong repellency for 30 minutes of exposure; then shifting to strong attractancy.

FIG. 8B is a series of graphs (showing the data as shown in FIG. 8A) depicted in three dimensions (in a rectangular mode for the "x" and "y" axes) showing the relative attractiveness or repellency of the $C_8$-t-alkanols and $C_5$–$C_{11}$-omega-alken-1-ols of our invention compared with a repellent, 1-nonen-3-ol, a known attractant, tagetone (concentration: 0.001% in triethyl citrate) and another known attractant, "extract of used fly rearing media" (mixture of manures, alfalfa and baking soda). The graphs are based on experiments run for a total of one hour with six intervals of 10 minutes each.

The graph indicated by reference numeral 108 is the graph for the compound 10-undecen-1-ol demonstrating strong repellency for 30 minutes of exposure; then shifting to a strong attractancy. The graph indicated by reference numeral 101 is the graph for the compound 3-ethyl-2-methyl-3-pentanol, an attractant. The graph indicated by reference numeral 102 is the graph for the compound 9-decen-1-ol. The graph indicated by reference numeral 103 is the graph for the compound 1-nonen-3-ol, a repellent. The graph indicated by reference numeral 104 is the graph for the standard attractant, "extract of used fly rearing media". The graph indicated by reference numeral 105 is the graph for the compound 3-ethyl-3-hexanol, an attractant. The graph indicated by reference numeral 106 is the graph showing the number of insects collected over time when no compound is used in the airstream in the apparatus of FIG. 1. The graph indicated by reference numeral 107 is the graph for the compound tagetone at a concentration of 0.001% in triethyl citrate (tagetone being an attractant). The graph indicated by reference numeral 118 is the graph for the compound 10-undecen-1-ol demonstrating a strong repellency for 30 minutes of exposure; then shifting to a strong attractancy. The graph indicated by reference numeral 111 is the graph for the compound 3-ethyl-2-methyl-3-pentanol, an attractant.

FIG. 9C depicts, graphically, a replicate of the data depicted in the graphs of FIGS. 9A and 9B; FIG. 9C being a series of graphs depicted in three dimensions (in a circular mode for the "x" and "y" axes) showing the relative attractiveness or repellency of the $C_8$-t-alkanols and $C_5$–$C_{11}$-omega-alken-1-ols of our invention compared with a repellent, 1-nonen-3-ol, a known attractant, tagetone (0.001% in triethyl citrate) and another known attractant, extract of used fly rearing media"(a mixture of manures, alfalfa and baking soda).

The graph indicated by reference numeral 121 is the graph for 3-ethyl-2-methyl-3-pentanol.

FIG. 9D is the series of graphs as set forth in FIGS. 9A and 9C, depicted in two dimensions. The graphs indicated by reference numerals 131A and 131B are the graphs for 3-ethyl-2-methyl-3-pentanol, an attractant. The graphs indicated by reference numerals 132A and 132B are for 9-decen-1-ol, an attractant. The graphs indicated by reference numerals 133A and 133B are the graphs for 1-nonen-3-ol, a repellent. The graphs indicated by reference numerals 134A and 134B are the graphs for the standard attractant, "extract of used fly rearing media". The graphs indicated by reference numerals 135A and 135B are the graphs for 3-ethyl-3-hexanol. The graphs indicated by reference numerals 136A and 136B are the graphs for number of *Musca domestica* L. (Diptera:Muscidae) collected over a period of time when no compound is used in the airstream when operating the apparatus of FIG. 1. The graphs indicated by reference numerals 137A and 137B are the graphs for tagetone at a concentration of 0.001% in triethyl citrate, a known attractant. The graphs indicated by reference numerals 138A and 138B are for 10-undecen-1-ol, demonstrating a strong repellency for 30 minutes of exposure; and then shifting to a strong attractancy.

FIG. 10A is a series of graphs, depicted in three dimensions (in a circular mode for the "x" and "y" axes) showing the relative attractiveness or repellency of the $C_8$-t-alkanols and $C_5$–$C_{11}$-omega-alken-1-ols of our invention compared with a repellent, 1-nonen-3-ol, a known attractant, tagetone (0.001% in triethyl citrate) and another known attractant, "extract of used fly rearing media" (a mixture of manures, alfalfa and baking soda). The graphs are based on experiments run for a total of two hours with six intervals of 20 minutes each. The results are tabulated in Table V as follows:

TABLE V

| Channel | Sample Code | Insects Per Interval | | | | | |
| --- | --- | --- | --- | --- | --- | --- | --- |
| channel 141 | sample D | 0 | 0 | 4 | 0 | 0 | 0 | 0 |
| channel 142 | sample G | 0 | 18 | 25 | 8 | 2 | 0 | 11 |
| channel 143 | sample E | 0 | 0 | 0 | 0 | 0 | 0 | 0 |
| channel 144 | sample F | 0 | 4 | 2 | 5 | 6 | 0 | 27 |
| channel 145 | sample C | 0 | 0 | 0 | 0 | 2 | 8 | 0 |
| channel 146 | sample H | 0 | 0 | 2 | 1 | 4 | 12 | 97 |
| channel 147 | sample A | 0 | 58 | 61 | 24 | 113 | 53 | 10 |
| channel 148 | sample B | 0 | 4 | 2 | 31 | 4 | 42 | 0 |

The graph indicated by reference numeral 141 is the graph for 3-ethyl-2-methyl-3-pentanol. The graph indicated by reference numeral 142 is the graph for 9-decen-1-ol, an attractant. The graph indicated by reference numeral 143 is the graph for 1-nonen-3-ol, a repellent. The graph indicated by reference numeral 144 is the graph for the standard attractant, "extract of used fly rearing media". The graph indicated by reference numeral 145 is the graph for 3-ethyl-3-hexanol, an attractant. The graph indicated by reference numeral 146 is the graph for 10-undecen-1-ol, demonstrating strong repellency for 30 minutes of exposure, then shifting to a strong attractancy. The graph indicated by reference numeral 147 is the graph for number of insects collected over a period of time when using no compound in the airstream on operation of the apparatus of FIG. 1.

The graph indicated by reference numeral 148 is the graph for the known attractant, tagetone at a concentration of 0.001% in triethyl citrate.

FIG. 10B is a series of graphs depicted in rectangular mode for the "x" and "y" axes showing the relative attractiveness or repellency of the $C_8$-t-alkanols and $C_5$–$C_{11}$-omega-alken-1-ols of our invention compared with a repellent, 1-nonen-3-ol, a known attractant, tagetone (0.001% in triethyl citrate) and another known attractant, "extract of used fly rearing media" (a mixture of manures, alfalfa and baking soda). The graphs are based on experiments run for a total of two hours at intervals of 20 minutes each. The results are tabulated in Table V, supra.

The graph indicated by reference numeral 158 is the graph for tagetone, a known attractant in 0.001% triethyl citrate. The graph indicated by reference numeral 151 is for 3-ethyl-2-methyl-3-pentanol, an attractant. The graph indicated by reference numeral 152 is for 9-decen-1-ol, an attractant. The graph indicated by reference numeral 153 is for 1-nonen-3-ol, a repellent. The graph indicated by reference numeral 154 is for the standard attractant, "extract of used fly rearing media". The graph indicated by reference numeral 155 is for 3-ethyl-3-hexanol, an attractant. The graph indicated by reference numeral 156 is for 10-undecen-1-ol demonstrating strong repellency for 30 minutes of exposure, then shifting to a strong attractancy. The graph indicated by reference numeral 157 indicates number of insects collected over a period of time with no compound in the airstream of the apparatus of FIG. 1. The graph indicated by reference numeral 158 is for tagetone, the known attractant at 0.001% concentration in triethyl citrate. The graph indicated by reference numeral 161 is for 3-ethyl-2-methyl-3-pentanol, an attractant.

FIG. 10C depictes a replicate of the data depicted graphically in FIG. 10A. The graph indicated by reference numeral 171 is the graph for the compound 3-ethyl-2-methyl-3pentanol, an attractant. The graph indicated by reference numeral 172 is for 9-decen-1-ol, an attractant. The graph indicated by reference numeral 173 is for 1-nonen-3-ol, a repellent. The graph indicated by reference numeral 174 is for the standard attractant, "extract of used fly rearing media". The graph indicated by reference numeral 175 is for 3-ethyl-3-hexanol, an attractant. The graph indicated by reference numeral 176 is for 10-undecen-1-ol demonstrating strong repellency for 30 minutes of exposure; then shifting to a strong attractancy. The graph indicated by reference numeral 177 measures number of insects collected over the entire period of time when using no compound in the airstream on operation of the apparatus of FIG. 1. The graph indicated by reference numeral 178 is for the known attractant, tagetone at 0.001% concentration in triethyl citrate.

FIG. 10D is the series of graphs of FIGS. 10A and 10C depicted graphically in two dimensions.

The graphs indicated by reference numeral 181 are for 3-ethyl-2-methyl-3-pentanol, an attractant. The graphs indicated by reference numerals 182A and 182B are for 9-decen-1-ol. The graph indicated by reference numeral 183 are for 1-nonen-3-ol, a repellent. The graphs indicated by reference numerals 184A and 184B are for the standard attractant "extract of used fly rearing media". The graphs indicated by reference numerals 185A and 185B are for 3-ethyl-3-hexanol, an attracant. The graphs indicated by reference numerals 186A and 186B are for 10-undecen-1-ol demonstrating strong repellency for 30 minutes of exposure; then shifting to a strong attractancy. The graphs indicated by reference numerals 187A and 187B measure number of insects collected over a period of time when using no compound in the airstream on operation of the apparatus of FIG. 1. The graphs indicated by reference numerals 188A and 188B are for the known attractant, tagetone at a level of 0.001% in triethyl citrate.

FIG. 11A is a series of graphs depicted in three dimensions (in a circular mode for the "x" and "y" axes) showing the relative attractiveness or repellency of the $C_8$-t-alkanols and $C_5$–$C_{11}$-omega-alken-1-ols of our inventon compared with a repellent, 1-nonen-3-ol a known attractant, tagetone (at 0.001% concentration in triethyl citrate) and another known attractant, "extract of used fly rearing media" (mixtures of manures, alfalfa and baking soda). The graphs are based on experiments run for a total of 6 hours with six intervals of one hour each. The results are tabulated in Table VI below as follows:

TABLE VI

| Channel | Sample Code | Insects Collected Per Interval | | | | | |
|---|---|---|---|---|---|---|---|
| channel 201 | sample D | 0 | 4 | 0 | 27 | 9 | 4 | 3 |
| channel 202 | sample G | 0 | 51 | 14 | 6 | 10 | 31 | 20 |
| channel 203 | sample E | 0 | 0 | 1 | 0 | 0 | 0 | 3 |
| channel 204 | sample F | 0 | 11 | 58 | 6 | 10 | .14 | 6 |
| channel 205 | sample C | 0 | 0 | 17 | 5 | 13 | 11 | 18 |
| channel 206 | sample H | 0 | 3 | 129 | 42 | 24 | 29 | 33 |
| channel 207 | sample A | 0 | 143 | 195 | 30 | 39 | 50 | 82 |
| channel 208 | sample B | 0 | 37 | 50 | 1 | 118 | 18 | 10 |

The graph represented by reference numeral 201 is the graph for 3-ethyl-2-methyl-3-pentanol, an attractant. The graph indicated by reference numeral 202 is the graph for 9-decen-1-ol, an attracant. The graph indicated by reference numeral 203 is the graph for 1-nonen-3-ol, a repellent. The graph indicated by reference numeral 204 is the graph for the standard attractant, "extract of used fly rearing media". The graph indicated by reference numeral 205 is the graph for 3-ethyl-3-hexanol, an attractant. The graph indicated by reference numeral 206 is the graph for 10-undecen-1-ol demonstrating strong repellency for 30 minutes of exposure; then shifting to a strong attractancy. The graph indicated by reference numeral 207 indicates number of insects collected over the entire period of time when using no compound in the airstream on operation of the apparatus of FIG. 1. The graph indicated by reference numeral 208 is for the known attractant, tagetone at a concentration of 0.001% in triethyl citrate.

FIG. 11B is a series of graphs depicted in three dimensions (in a rectangular mode for the "x" and "y"

axes) showing the relative attractiveness or repellency of the C$_8$-t-alkanols and C$_5$-C$_{11}$-omega-alken-1-ols of our invention compared with a repellent, 1-nonen-3-ol, a known attractant, tagetone (0.001% in triethyl citrate) and another known attractant, "extract of used fly rearing media" (a mixture of manures, alfalfa and baking soda). The graphs are based on experiments run for a total of 6 hours at six intervals of one hour each. The results are tabulated in Table VI, supra.

The graph indicated by reference numeral 218 is the graph for the known attractant, tagetone at a concentration of 0.001% in triethyl citrate. The graph indicated by reference numeral 211 is the graph for 3-ethyl-2-methyl-3-pentanol, an attractant. The graph indicated by reference numeral 212 is the graph for 9-decen-1-ol, an attractant. The graph indicated by reference numeral 213 is the graph for 1-nonen-3-ol, a repellent. The graph indicated by reference numeral 214 is the graph for the standard attractant, "extract of used fly rearing media". The graph indicated by reference numeral 215 is the graph for 3-ethyl-3-hexanol, an attractant. The graph indicated by reference numeral 216 is the graph for 10-undecen-1-ol demonstrating strong repellency for 20 minutes of exposure, then shifting to a strong attractancy. The graph indicated by reference numeral 217 is the graph showing number of insects collected over the entire period of 6 hours when using no compound in the airstream on operation of the apparatus of FIG. 1. The graph indicated by reference numeral 228 is the graph for the known attractant, tagetone at a concentration of 0.001% in triethyl citrate. The graph indicated by reference numeral 221 is the graph for 3-ethyl-2-methyl-3-pentanol, an attractant.

FIG. 11C depictes a replicate of the data graphically depicted in FIG. 11A. FIG. 11C is also a series of graphs depicted in three dimensions in a circular mode for the "x" and "y" axes.

The graph indicated by reference numeral 231 is the graph for 3-ethyl-2-methyl-3-pentanol, an attractant. The graph indicated by reference numeral 232 is the graph for 9-decen-1-ol, an attractant. The graph indicated by reference numeral 233 is the graph for 1-nonen-3-ol, a repellent. The graph indicated by reference numeral 234 is for the standard attractant, "extract of used fly rearing media". The graph indicated by reference numeral 235 is the graph for 3-ethyl-3-hexenol, an attractant. The graph indicated by reference numeral 236 is for 10-undecen-1-ol demonstrating strong repellency for 10 minutes of exposure, then shifting to a strong attractancy. The graph indicated by reference numeral 237 indicates number of insects collected over the entire period of 6 hours of measurement when using no compound in the airstream on operation of the apparatus of FIG. 1. The graph indicated by reference numeral 238 is the graph for the known attractant, tagetone at a concentration of 0.001% in triethyl citrate.

FIG. 11D is a series of graphs of FIGS. 11A and 11C depicted in two dimensions.

The graphs indicated by reference numerals 241A and 241D are for 3-ethyl-2-methyl-3-pentanol, an attractant. The graphs indicated by reference numerals 242A and 242B are for 9-decen-1-ol, an attractant. The graph indicated by reference numeral 243 is for 1-nonen-3-ol, a repellent. The graphs indicated by reference numerals 244A and 244B are for the standard attractant "extract of used fly rearing media". The graphs indicated by reference numerals 245A and 245B are for 3-ethyl-3-hexanol, an attractant. The graphs indicated by reference numerals 246A and 246B are for 10-undecen-1-ol demonstrating strong repellency for 10 minutes of exposure, then shifting to a strong attractancy. The graphs indicated by reference numerals 247A and 247B indicate number of insects collected over a period of time when no compound is used in the airstream on operation of the apparatus of FIG. 1. The graphs indicated by reference numerals 248A and 248B are for the known attractant, tagetone at a level of 0.001% in triethyl citrate.

Figure 12:
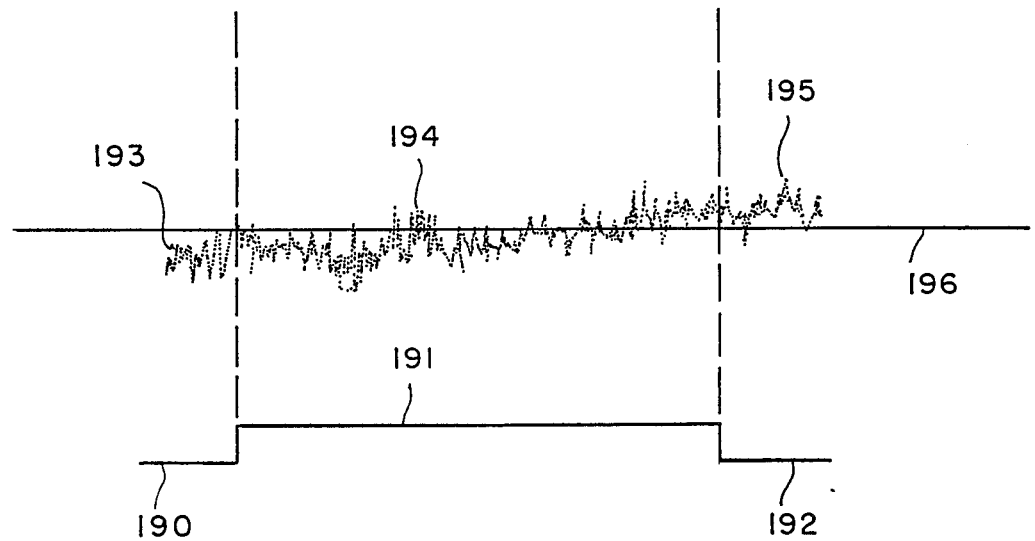
FIG. 12 is a graph of neural signal vs. time recorded from the antennal lobe of the house fly (*Musca domestica L.* (Diptera:Muscidae)) using the attractant called "extract of used fly rearing media" (mixture of manures, alfalfa and baking soda) as the stimulus.

Referring to FIG. 12, FIG. 12 sets forth the neural signal recorded from the antennal lobe of *Musca domestica L.* (Diptera:Muscidae) using the attractant called "Extract of used fly rearing media" as described, supra. Passage of the attractant to the *Musca domestica L.* (Diptera:Muscidae) is indicated at reference numeral 191 whereas reference numerals 190 and 192 indicate no passage of the treating material to be tested. When passage of the test material takes place the neural signal is indicated at reference numeral 194. When there is no passage of the test material the neural signal is indicated at reference numerals 193 and 195. Reference numeral 196 is the base line for the neural signal recorded from the antennal lobe using the attractant called "Extract of used fly rearing media". The lack of any change from the base line during treatment (191) is indicative of the fact that the "Extract of used fly rearing media" is a strong attractant for *Musca domestica L.* (Diptera:Muscidae).

Figure 13:
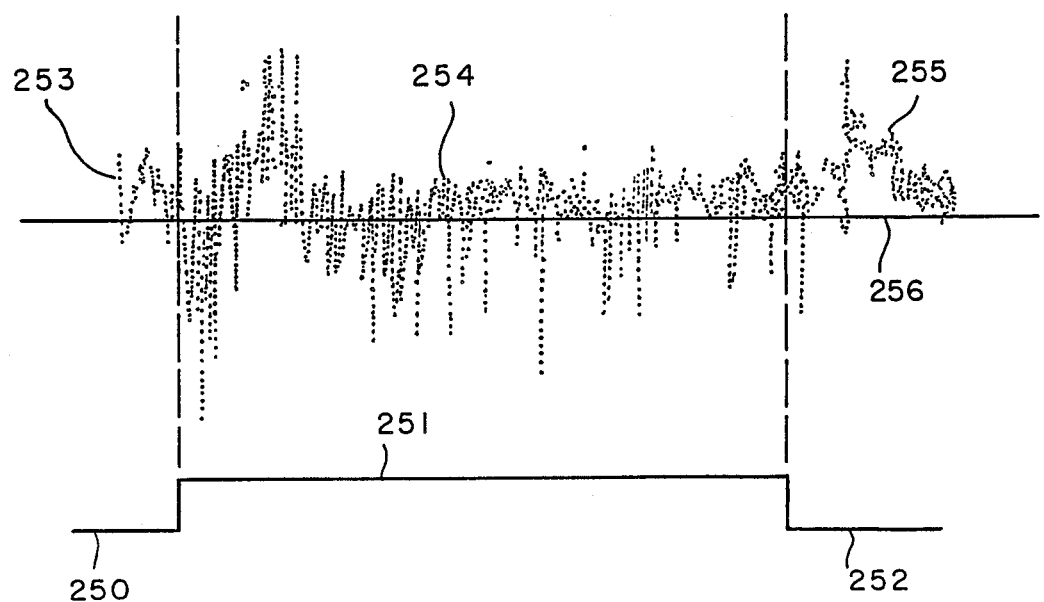
FIG. 13 is a graph of the neural signal vs. time recorded from the antennal lobe of the *Musca domestica L.* (Diptera:Muscidae)(house fly) using the attractant 2,3-dimethyl-3-hexanal as the stimulus.

FIG. 13 sets forth the neural signal recorded from the antennal lobe of the *Musca domestica L.* (Diptera:Muscidae) using the attractant 2,3-dimethyl-3-hexanol. The neural signal in FIG. 13 is set forth and is shown using reference numerals 253, 254 and 255 and the passage or treatment period is shown using reference numerals 250, 251 and 252. Reference numerals 250 and 252 show no passage of test material, e.g., 2,3-dimethyl-3-hexanol. The neural signal recorded when no passage of test material takes place is set forth at reference numerals 253 and 255 (respectively for periods 250 and 252). The neural signal recorded when test material is used to treat the *Musca domestica L.* (Diptera:Muscidae) is set forth at reference numeral 254. The base line for the neural signal recorded from the antennal lobe using 2,3-dimethyl-3-hexnol is indicated by reference numeral 256. The lack of change from the base line during treatment (251) is indicative of the fact that the 2,3-dimethyl-3-hexanol is a strong attractant for *Musca domestica L.* (Diptera:Muscidae).

Figure 14:
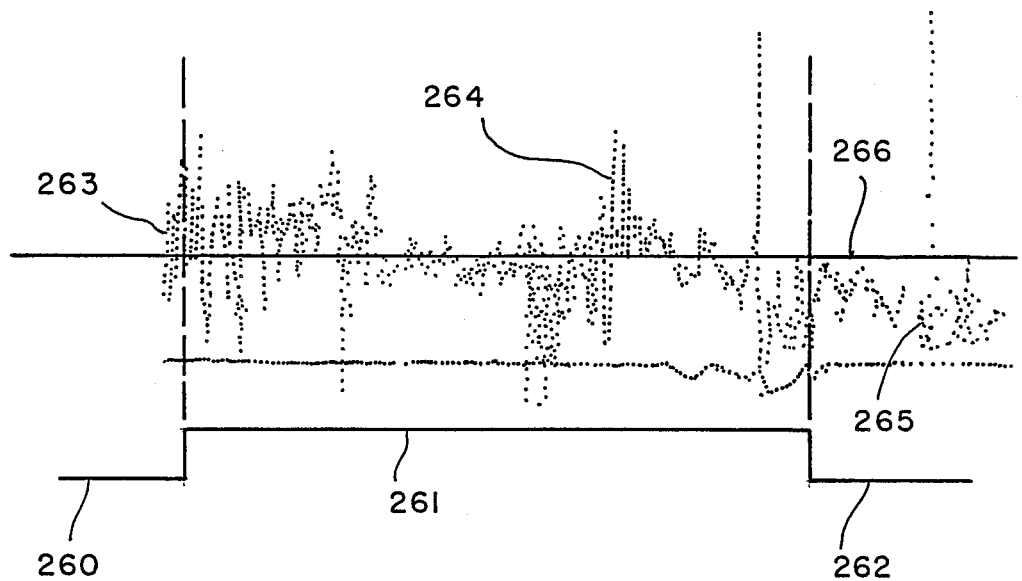
FIG. 14 is graph of neural signal vs. time recorded from the antennal lobe of the *Musca domestica L.* (Diptera:Muscidae) (house fly) using the attractant 3-ethyl-2-methyl-3-pentanol as the stimulus.

FIG. 14 sets forth the neural signal recorded from the antennal lobe of the *Musca domestica L.* (Diptera:Muscidae) using 3-ethyl-2-methyl-3-pentanol. The neural signal in FIG. 14 is set forth and is shown using reference numerals 263, 264 and 265 and the passage or treatment period is shown using reference numerals 260, 261 and 262. Reference numerals 260 and 262 show no passage of the test material, the 3-ethyl-2-methyl-3-pentenol. The neural signal recorded when no passage of test material takes place is set forth at reference numerals 263 and 265 (respectively, for periods 260 and 262). The neural signal recorded when test material is used to treat the *Musca domestica L.* (Diptera:Muscidae) is set forth at reference numeral 264. The base line for the neural signal recorded from the antennal lobe using 3-ethyl-2-methyl-3-pentanol is indicated by reference numeral 266. The lack of change from the base line during treatment (261) is indicative of the fact that the 3-ethyl-2-methyl-3-pentanol is a strong attractant for *Musca domestica L.* (Diptera:Muscidae).

Figure 15:
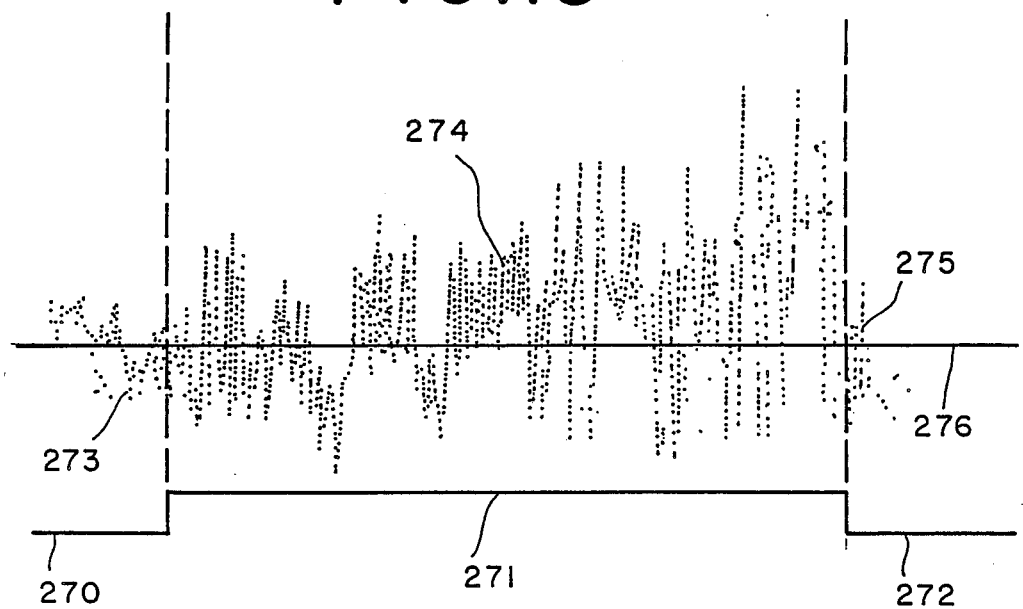
FIG. 15 is graph of neural signal vs. time recorded from the antennal lobe of the *Musca domestica L.* (Diptera:Muscidae) (house fly) using the attractant 3-ethyl-3-hexanal as the stimulus.

FIGS. 15 sets forth the neural signals recorded from the antennal lobes of the *Musca domestica L.* (Diptera:Muscidae) using 3-ethyl-3-hexanol. The neural signal in FIG. 15 is set forth and is shown using reference numerals 273, 274 and 275 and the passage or treatment period is shown using reference numerals 270, 271 and 272. Reference numerals 270 and 273 show no passage of test material, e.g., 3-ethyl-3-hexanol. The neural signal recorded when no passage of test material takes place is set forth at reference numerals 273 and 275 (respectively, for periods 270 and 272). The neural signal recorded when test material is used to treat the *Musca domestica L.* (Diptera:Muscidae) is set forth at reference numeral 274. The base line for the neural signal recorded from by the antennal lobe using 3-ethyl-3-hexanol is indicated by reference numeral 276. The lack of change from the base line during treatment (271) is indicative of the fact that the 3-ethyl-3-hexanol is a strong attractant for *Musca domestica L.* (Diptera:Muscidae).

Figure 16:
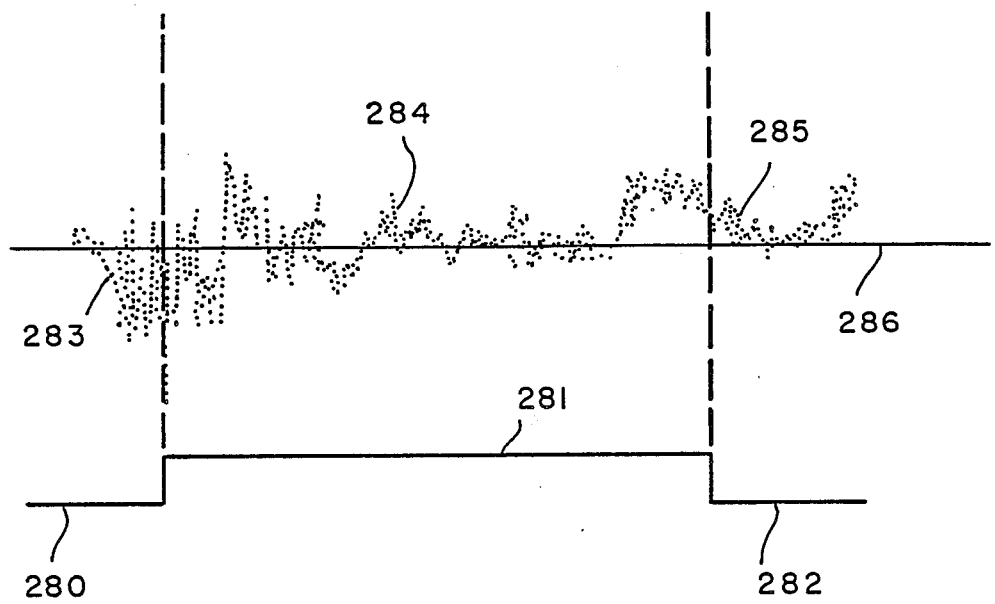
FIG. 16 is a graph of the neural signal vs. time recorded from the antennal lobe of the *Musca domestica L.* (Diptera:Muscidae) (house fly) using the attractant 3-methyl-3-buten-1-ol as the stimulus.

FIG. 16 sets forth the neural signals recorded from the antennal lobes of the *Musca domestica L.* (Diptera:Muscidae) using 3-methyl-3-buten-1-ol. The neural signal in FIG. 16 is set forth and is shown using reference numerals 283, 284 and 285 and the passage or treatment period is shown using reference numerals 280, 281 and 282. Reference numerals 280 and 282 show no passage of the test material, 3-methyl-3-buten-1-ol. The neural signal recorded when no passage of test material takes place as set forth at reference numerals 283 and 285 (respectively for periods 280 and 282). The neural signal recorded when test material is used to treat the *Musca domestica L.* (Diptera:Muscidae) is set forth at reference numeral 284. The base line for neural signal recorded from the antennal lobe using 3-methyl-3-buten-1-ol is indicated by reference numeral 286. The lack of change from the base line during treatment (281) is indicative of the fact that the 3-methyl-3-buten-1-ol is a strong attractant for *Musca domestica L.* (Diptera:Muscidae).

The neural signal in FIG. 16 is set forth and is shown using reference numerals 283, 284 and 285 and the passage or treatment period is shown using reference numerals 280, 281 and 282. Reference numerals 280 and 282 show no passage of the test material, e.g., 3-methyl-3-buten-1-ol. The neural signal recorded when no passage of test material takes place is set forth at reference numerals 283 and 285 (respectively, for periods 280 and 282). The neural signal recorded when test material is used to treat the *Musca domestica L.* (Diptera:Muscidae) is set forth at reference numeral 284. The base line for neural signal recorded from the antennal lobe using 3-methyl-3-buten-1-ol is indicated by reference numeral 286. The slight variable change from the base line during treatment (281) is indicative of the fact that the 3-methyl-3-buten-1-ol is a marginal attractant for *Musca domestica L.* (Diptera:Muscidae).

This compound appears to be dosage dependent and appears initially as a repellant, shifting to a good attractant.

Figure 17:
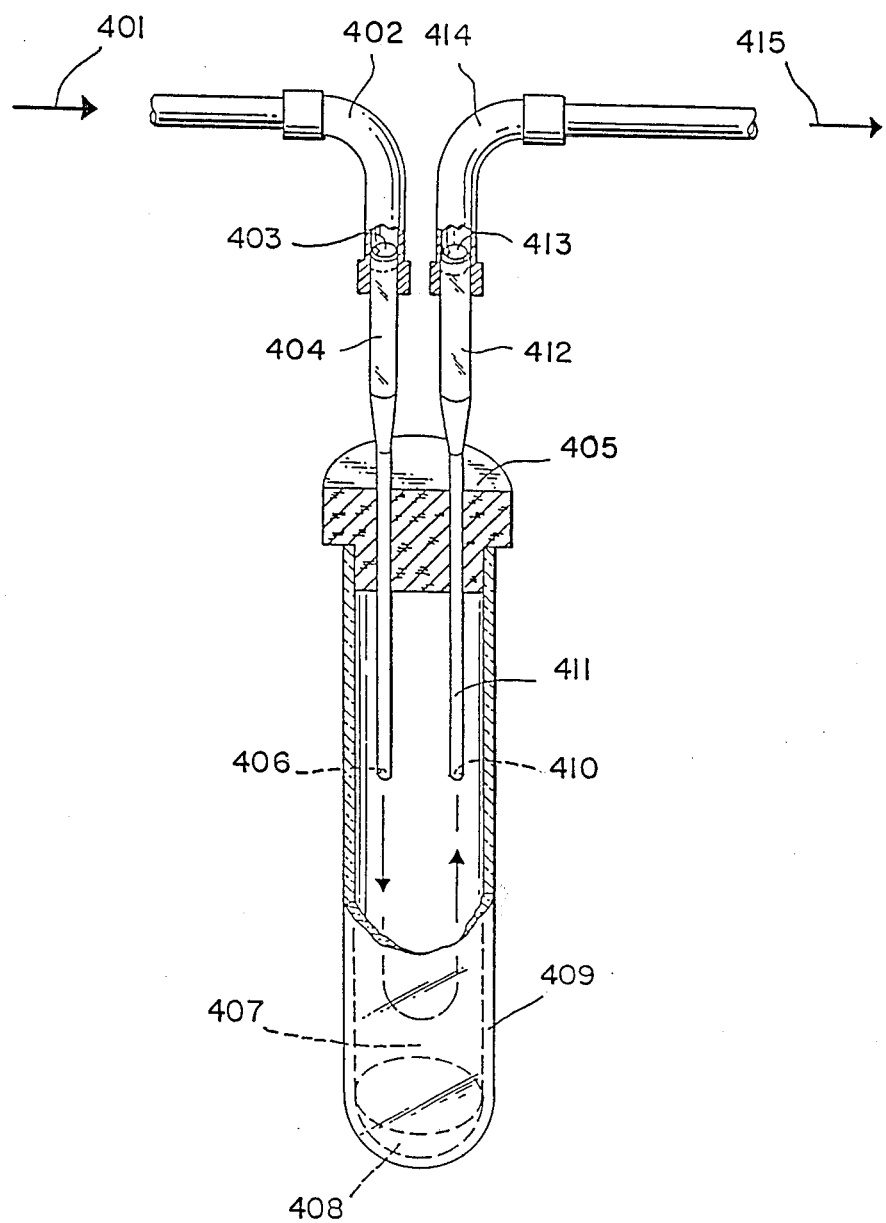
FIG. 17 is a perspective view of the odor delivery system used to supply odor to the house fly (*Musca domestica L.* (Diptera:Muscidae)) when collecting data from the electrophysiological study of the neural correlates of attraction and repulsion in the house fly (*Musca domestica L.* (Diptera:Muscidae)).

FIG. 17 is a diagram in perspective, of an odor delivery system used to supply such materials as 3-ethyl-2-methyl-3-pentanol to the fly. When applying the attractant or repellent to be tested to the fly, air from a pressurized tank is fed through line 401 at location 402 through a valve through pipette 403/404 through orifice 406 into tube 409 containing the media to be tested, e.g., 3-ethyl-2-methyl-3-pentanol, indicated by reference numeral 408. The headspace 407 over the media 408 will thus include molecules of air as well as the material to be tested, e.g., 3-ethyl-2-methyl-3-pentanol. The resulting mixture of air and attractant or repellent is then passed through orifice 410 through tube 411-412-414 in direction 415 to the location where the fly (*Musca domestica L.* (Diptera:Muscidae)) reactions are being measured. Tubes 404 and 412 are held in place by holder 405.

The house flies used for this study were supplied from a laboratory colony at the medical and veterinary entomology laboratory at the University of Florida. A female, 3–7 day old fly was restrained on a standard microscope slide using the following technique. The fly's wings were clipped off near the base in order to facilitate handling. The fly was then glued to the microscope slide, dorsal side down, using Super glue ™. Ski wax was melted around the head capsule to immobilize the head during electrode penetration. The slide was then placed under a dissecting microscope to enable a more accurate placement of the electrode.

Microcapillary electrodes (tip O.D. 1–5 mm) were filled with an ionic fluorescent solution which served the dual purpose of a conducting solution as well as marking the recording site. The ionic solution contained Lucifer yellow CH, a superfluorescent lithium salt of 3,6-disulphonate 4-aminonaphthalimide (Stewart, W. W. 1978 "Functional connections between cells as revealed by dye-coupling with a highly fluorescent naphthalimide tracer" Cell 14:741–759), which is taken up by depolarizing neurons via induced endocytosis (Wilcox and Franceschini, N. 1984 "Illumination induces dye incorporation in photoreceptor cells" Science (Washington, D.C.) 225:851–854.).

The active electrode was positioned in the selected spot using Nashike micromanipulators with remote hydraulic drive. Areas for electrophysiological study were located using (Strausfeld, N.J. 1978 "Atlas of an insect brain", Springer-Verlag:Berlin) (1976) detailed anatomical study of the house fly brain, which includes a three-dimensional coordinate system. Subsequent gross dissections showed that with much practice, individual lobes on the brain could be penetrated with repeatable accuracy.

The indifferent electrode was placed either in the head capsule or thorax. The preferred position was the thorax as this places the electrode out of the way. However, care must be taken not to place the indifferent electrode in the ventral nerve cord as this results in extraneous nerve signals.

In placing the active electrode, it was necessary to prick the cuticle with a minuten pin in order to prevent deformation of the head capsule as the electrode penetrated. This method minimized damage to the underlying neural tissue.

Nerve signals were preamplified with custom neutral amplifirs at 100X and then displayed on a Nicolet 3091 oscilloscope. The same signal was simultaneously sent to a Dianachart smart recorder/data logger to obtain a hard copy of the neural signal.

The olfactory stimulus was initially supplied using the technique developed by (Kauer, J. S.; Shepherd, G. M. 1975 "Olfactory stimulation and monitored step pulses of odor", Brain Res. 85:108–113) and (Getchel, T. V.; Shepherd, G. M. 1978 "Responses of olfactory receptor cells to step pulses of odor at different concentrations in the salamander", J. Physiol. 282:521–540)

which uses three concentric pipettes, one to apply the odor and the other two to exhaust the odor. However, this system proved to be too bulky for house flies due to their small size, as it was not possible to form three concentric pipettes which were small enough not to be bulky, but not so small as to restrict air flow.

Consequently, a system was developed which used pressurized air to deliver the odor and an exhaust system was built around the entire set up. The delivery system was a test tube containing 2 ml of odor extract, stoppered, and with two disposable pipettes through the rubber stopper (as is shown in FIG. 17). One pipette 404 was attached to a pressurized air tank and the other pipette 412 was attached to a tygon tube terminating in a capillary tube which could be positioned directly in front of the fly's antennae.

Odor delivery (e.g., delivery of 3-ethyl-2-methyl-3-pentanol) was controlled with a valve so that abrupt onset of the stimulus was possible. Each stimulus was approximately 4–5 seconds in duration. A minimum of 15 minutes was used between odor stimulus to allow the previous odor to be completely exhausted from the area.

When using the embodiment of our invention as set forth in FIGS. 3, 4 and 4A, the heating element is set at 36° C. and is run at 32°–36° C.

When using any of the embodiments of our invention, the air flow rate past the sensors, (e.g., sensor 610 in FIG. 3) is preferably 275 feet per minute at a temperature, preferably of 28° C. or 83° F.

When using heated apparatus as set forth in FIGS. 3, 4 and 5, it is preferable that the heating coils 662a and 662b have inside diameters of approximately 0.75 inches.

The embodiment of our invention set forth in detail in FIG. 5 (with no light being supplied to landing surfaces 710, 710a et seq.) is useful for determining attractancy and repellency of ticks because ticks feed in the dark and are attracted to a warm body. Accordingly, the use of the embodiment of FIG. 5 taken further together with the apparatus of FIGS. 3, 4 and 4a is preferred when testing ticks.

The apparatus of FIGS. 1 and 2A is preferred when testing for attractancy of flies and mosquitos. House flies (*Musca domestica*) require light and no heat for a normal life. Accordingly, the apparatus of FIGS. 1 and 2A without the use of the special heating equipment of FIGS. 3, 4 and 4A is preferred when testing *Musca domestica*.

Mosquitos require low light and heat when feeding. Accordingly, in testing mosquitos for attractancy and repellency the equipment of FIGS. 1 and 2A is supplemented by the special heating equipment of FIGS. 3, 4 and 4A.

What is claimed is:

1. A method of attracting *Musca domestica* L. (Diptera:Muscidae) comprising exposing a 3 dimensional space to a *Musca domestica* L. (Diptera:Muscidae)-attracting concentration and quantity of a composition of matter selected from the group consisting of:
   (i) $C_8$-t-alkanols; and
   (ii) $C_5$–$C_{11}$-Omega-alken-1-ols.

2. The method of claim 1 wherein the $C_8$-t-alkanols and $C_5$–$C_{11}$-Omega-alken-1-ols are selected from the group consisting of:
   (i) 9-decen-1-ol having the structure:

(ii) 10-undecen-1-ol having the structure:

(iii) 3-ethyl-3-hexanol having the struture:

(iv) 3-ethyl-2-methyl-3-pentanol having the structure:

(v) 2,3-dimethyl-3-hexanol having the structure:

(vi) 3-methyl-3-buten-1-ol having the structure:

3. The process of claim 1 wherein at least one of the $C_8$-t-alkanols and $C_5$–$C_{11}$-omega-alken-1-ols is imbedded in a polymer compatible with said $C_8$-t-alkanols and $C_5$–$C_{11}$-omega-alken-1-ols.

4. The method of claim 1 wherein the 3 dimensional space is exposed to 9-decen-1-ol.

5. The method of claim 1 wherein the 3 dimensional space is exposed to 10-undecen-1-ol having the structure:

6. The method of claim 1 wherein the 3-dimensional space is exposed to 3-ethyl-3-hexanol having the structure:

7. The method of claim 1 wherein the 3 dimensional space is exposed to 3-ethyl-2-methyl-3-pentanol having the structure:

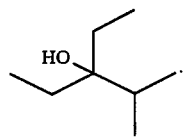

8. The method of claim 1 wherein the 3 dimensional space is exposed to 2,3-dimethyl-3-hexanol having the structure:

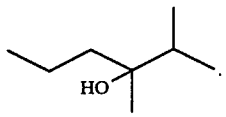

9. The method of claim 1 wherein the 3 dimensional space is exposed to 3-methyl-3-buten-1-ol having the structure:

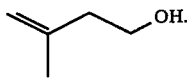

10. The process of claim 3 wherein the polymer compatible with said $C_8$-t-alkanols and $C_5$-$C_{11}$-omega-alken-1-ols is combined with said $C_8$-t-alkanols and $C_5$-$C_{11}$-omega-alken-1-ols by means of coextrusion.

11. An insect trap comprising a trap structure and contained therein a composition of matter selected from the group consisting of:
 (i) $C_8$-t-alkanols; and
 (ii) $C_5$-$C_{11}$-Omega alken-1-ols.

12. A method of first repelling *Musca domestica L.* (Diptera:Muscides) for a finite period of time in the range of from about 10 minutes up to about 30 minutes and then attracting said *Musca domestica L.* (Diptera:Muscidae) thereafter comprising the step of exposing a 3 dimensional space to a composition of matter consisting essentially of an alcohol selected from the group consisting of 10-undecen-1-ol having the structure:

and 3-methyl-3-buten-1-ol having the structure:

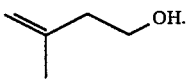

13. The process of claim 12 wherein the 10-undecen-1-ol and 3-methyl-3-buten-1-ol is imbedded in a polymer compatible with said 10-undecen-1-ol and 3-methyl-3-buten-1-ol and said polymer is coextruded with said 10-undecen-1-ol and said 3-methyl-3-buten-1-ol.

* * * * *